(12) United States Patent
Palme, Jr. et al.

(10) Patent No.: US 8,740,815 B2
(45) Date of Patent: Jun. 3, 2014

(54) GUIDEWIRE

(71) Applicant: Device Source, LLC, Lindstrom, MN (US)

(72) Inventors: Robert A. Palme, Jr., Lindstrom, MN (US); Gregory L. Townsend, Motley, MN (US)

(73) Assignee: Device Source LLC, Lindstrom, MN (US)

( * ) Notice: Subject to any disclaimer, the term of this patent is extended or adjusted under 35 U.S.C. 154(b) by 0 days.

(21) Appl. No.: 14/055,603

(22) Filed: Oct. 16, 2013

(65) Prior Publication Data

US 2014/0046216 A1    Feb. 13, 2014

Related U.S. Application Data

(63) Continuation of application No. 12/321,882, filed on Jan. 27, 2009.

(51) Int. Cl.
*A61B 5/00* (2006.01)
*A61M 25/00* (2006.01)

(52) U.S. Cl.
USPC .......................................... 600/585

(58) Field of Classification Search
USPC .......................................... 600/585
See application file for complete search history.

(56) References Cited

U.S. PATENT DOCUMENTS

| | | | |
|---|---|---|---|
| 3,521,620 A | 7/1970 | Cook | |
| 4,757,827 A | 7/1988 | Buchbinder et al. | |
| 4,798,598 A | 1/1989 | Bonello et al. | |
| 4,813,434 A | 3/1989 | Buchbinder et al. | |
| 4,815,478 A | 3/1989 | Buchbinder et al. | |
| 4,940,062 A | 7/1990 | Hampton et al. | |
| 5,037,391 A | 8/1991 | Hammerslag et al. | |
| 5,060,660 A | 10/1991 | Gambale et al. | |
| 5,120,308 A | 6/1992 | Hess | |
| 5,125,895 A | 6/1992 | Buchbinder et al. | |
| 5,203,772 A | 4/1993 | Hammerslag et al. | |
| 5,211,636 A | 5/1993 | Mische | |
| 5,372,587 A | 12/1994 | Hammerslag et al. | |
| 5,824,031 A | 10/1998 | Cookston et al. | |
| 6,059,739 A | 5/2000 | Baumann | |
| 6,126,649 A | 10/2000 | VanTassel et al. | |
| 6,146,338 A | 11/2000 | Gardeski et al. | |
| 6,776,765 B2 | 8/2004 | Soukup et al. | |
| 7,141,024 B2 | 11/2006 | Gaber | |
| 7,481,778 B2 | 1/2009 | Cedro et al. | |
| 2004/0102719 A1 | 5/2004 | Keith et al. | |
| 2006/0089569 A1 | 4/2006 | Soukup et al. | |

FOREIGN PATENT DOCUMENTS

| | | |
|---|---|---|
| GB | 1 119 158 | 7/1968 |
| WO | 92/14515 | 9/1992 |
| WO | 97/31677 | 9/1997 |

OTHER PUBLICATIONS

EPO Examination Report from corresponding EP application serial No. 20100736132.

*Primary Examiner* — Brian Szmal
*Assistant Examiner* — Megan Leedy
(74) *Attorney, Agent, or Firm* — Richard C. Emery; Mara E. DeBoe; Kagan Binder, PLLC

(57) ABSTRACT

A guidewire has a coil with a side of the coil winds having solid physical connections between the coil winds to prevent the connected coil wind side from expanding resulting from the application of force by an actuating member. The application of longitudinal force to the coil causes the unconnected coil wind side to expand while the connected side does not expand, resulting in the guidewire assuming a different configuration.

19 Claims, 28 Drawing Sheets

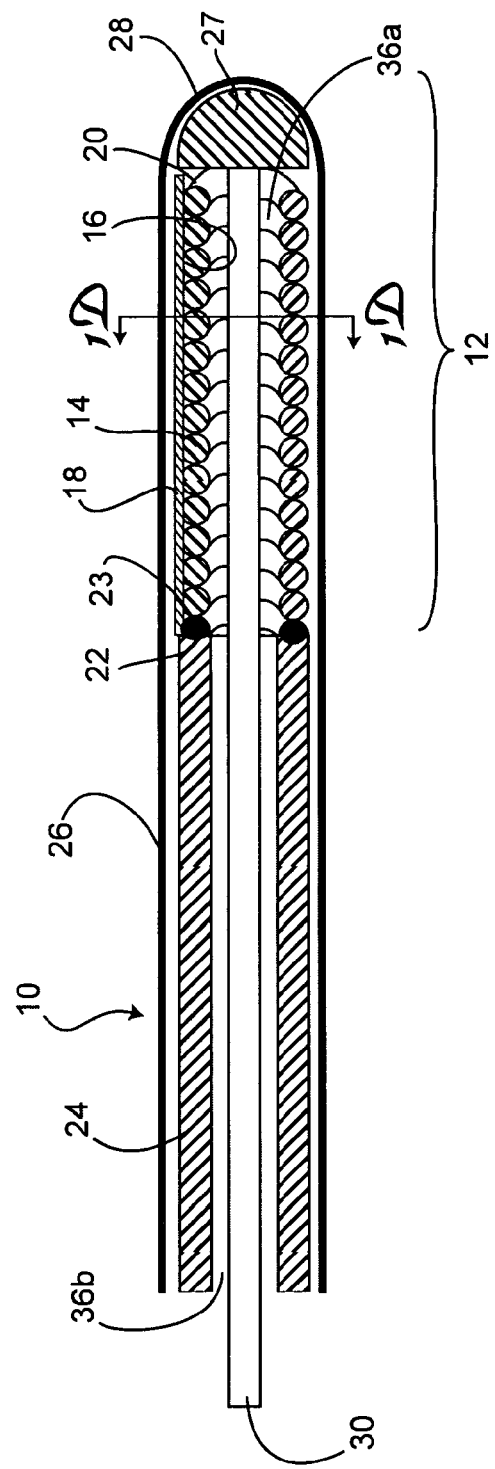

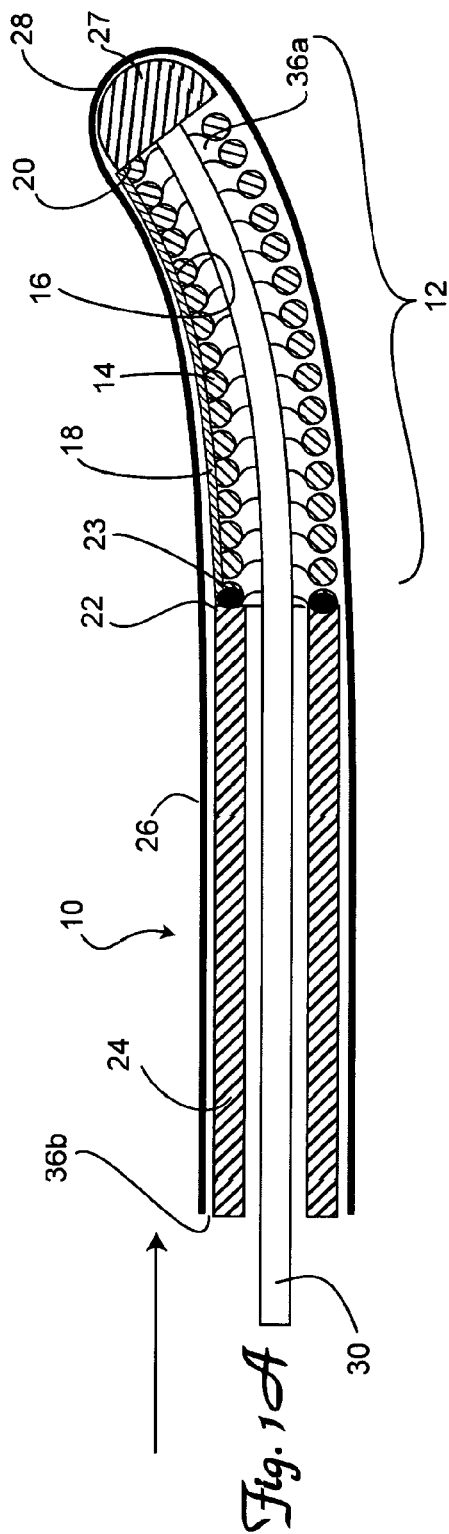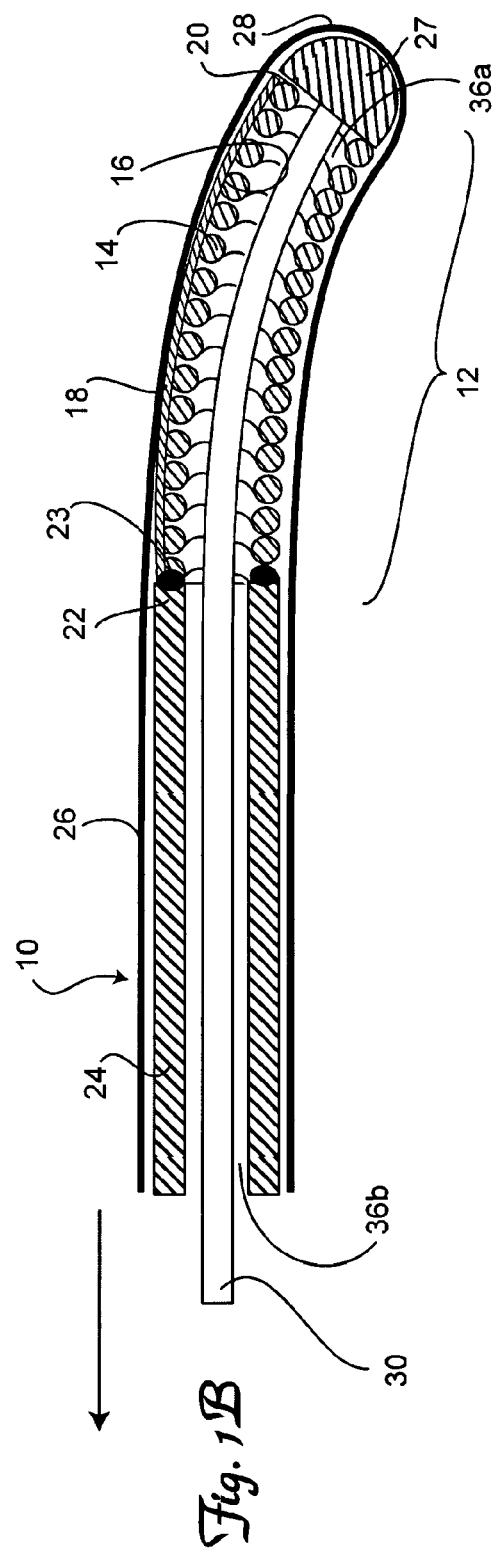

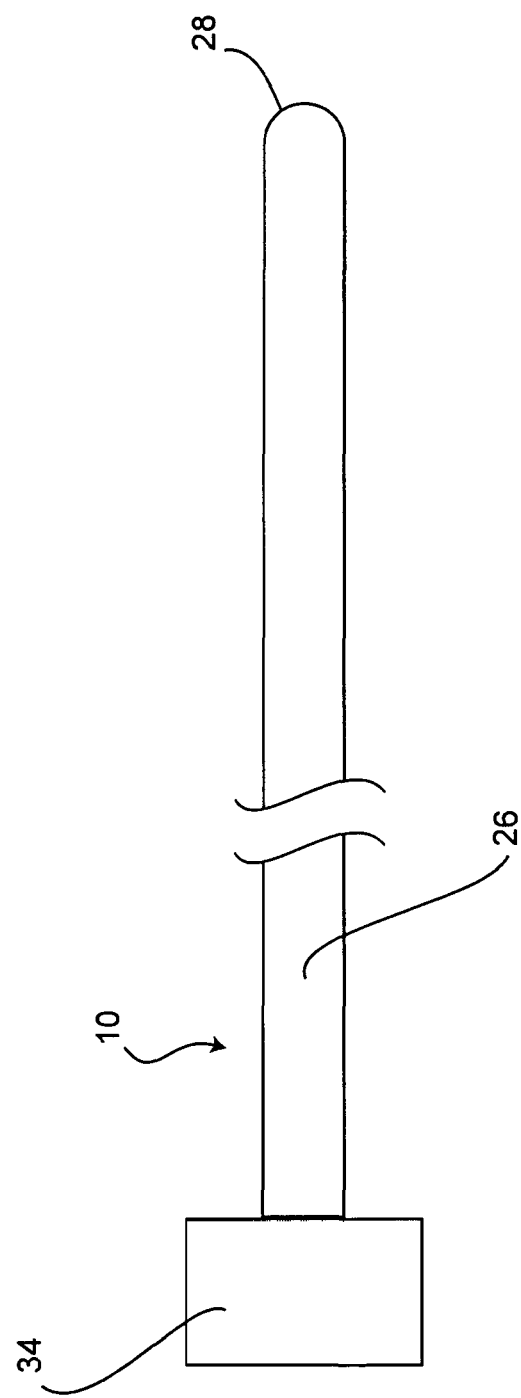

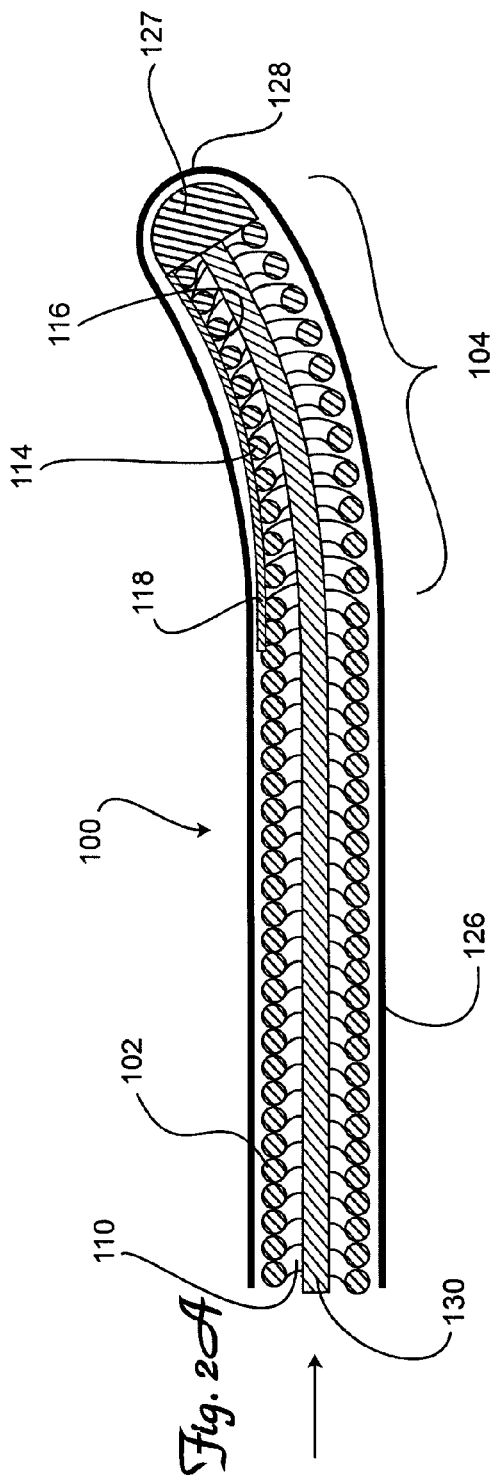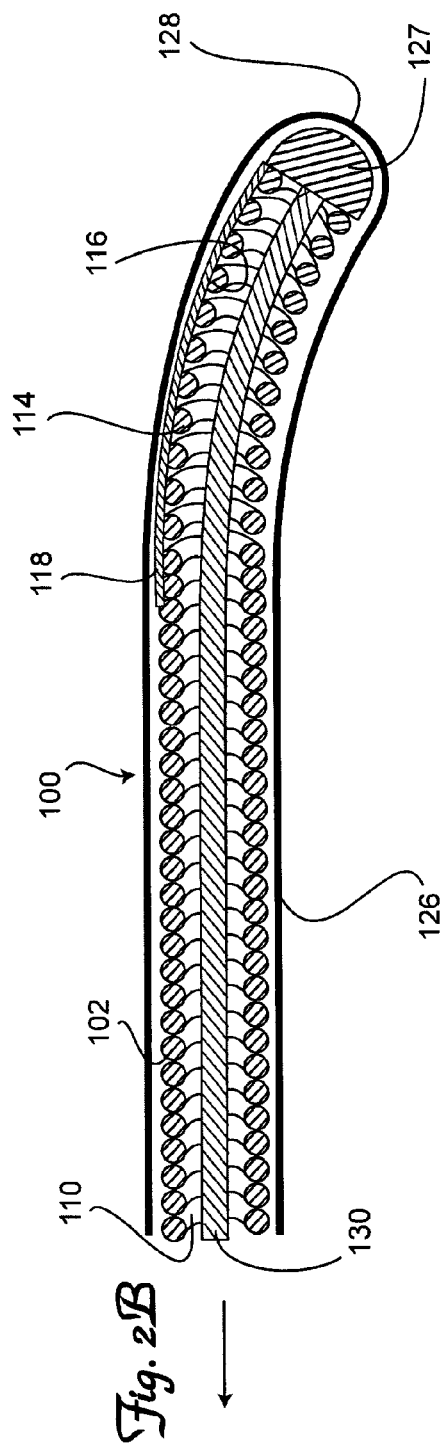

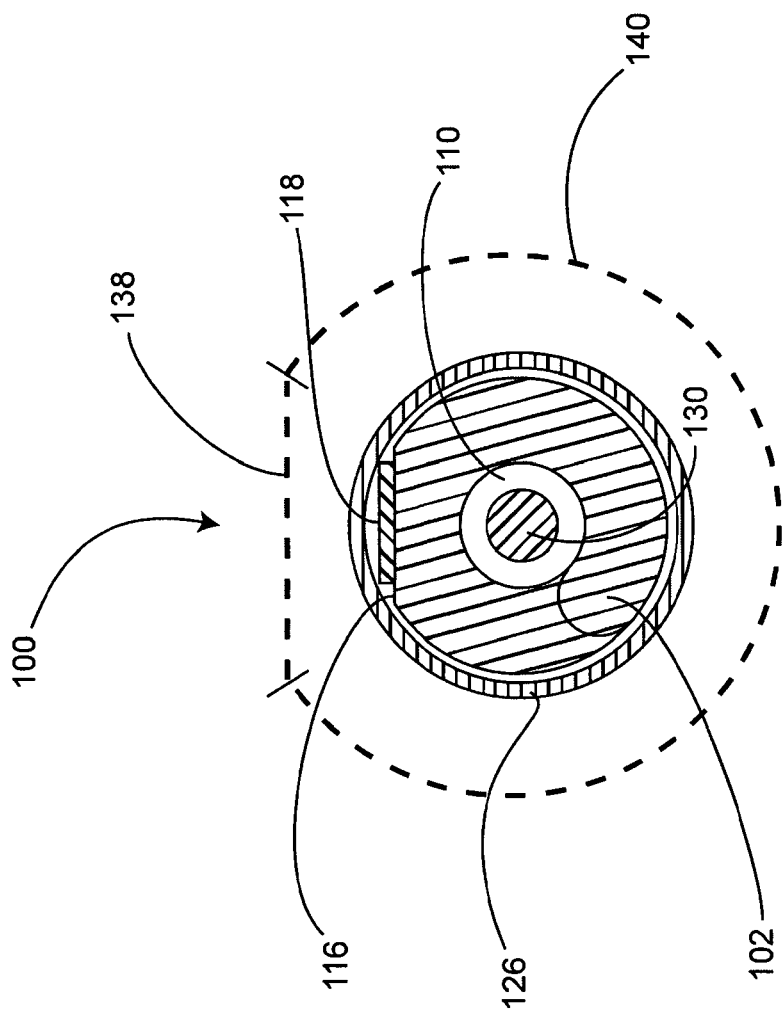

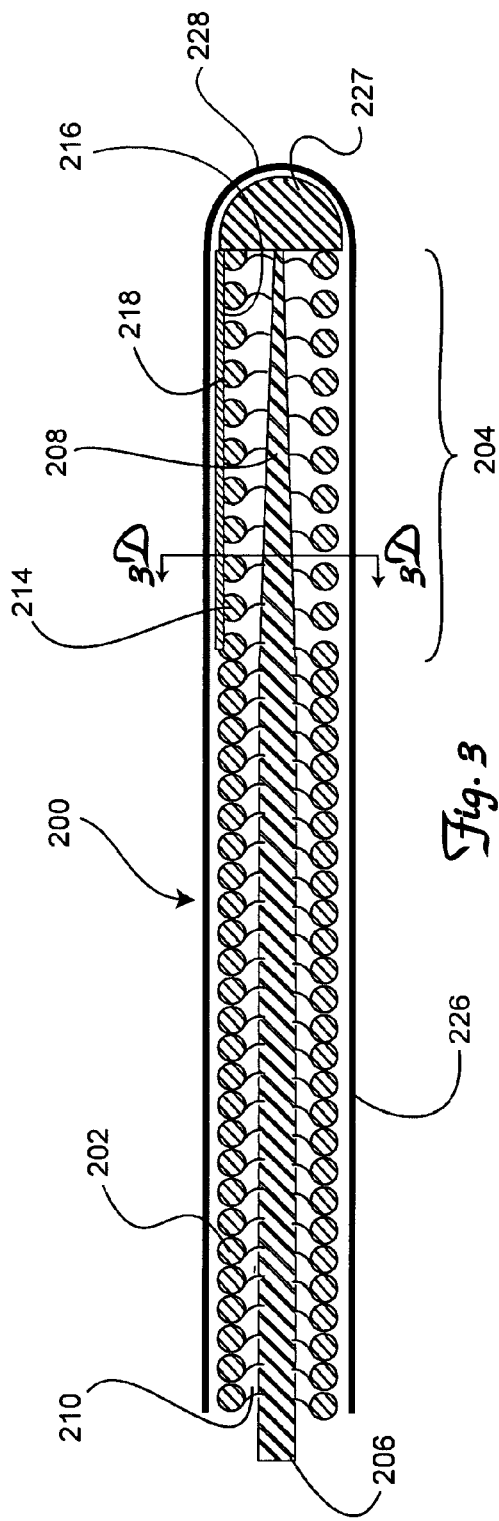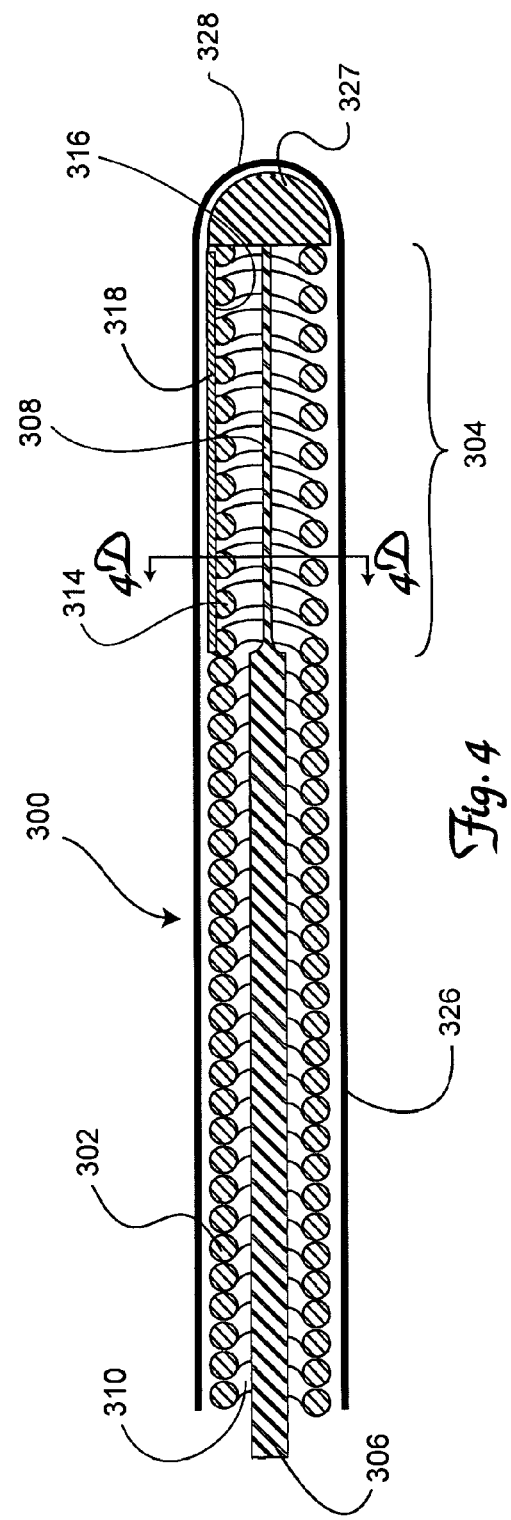

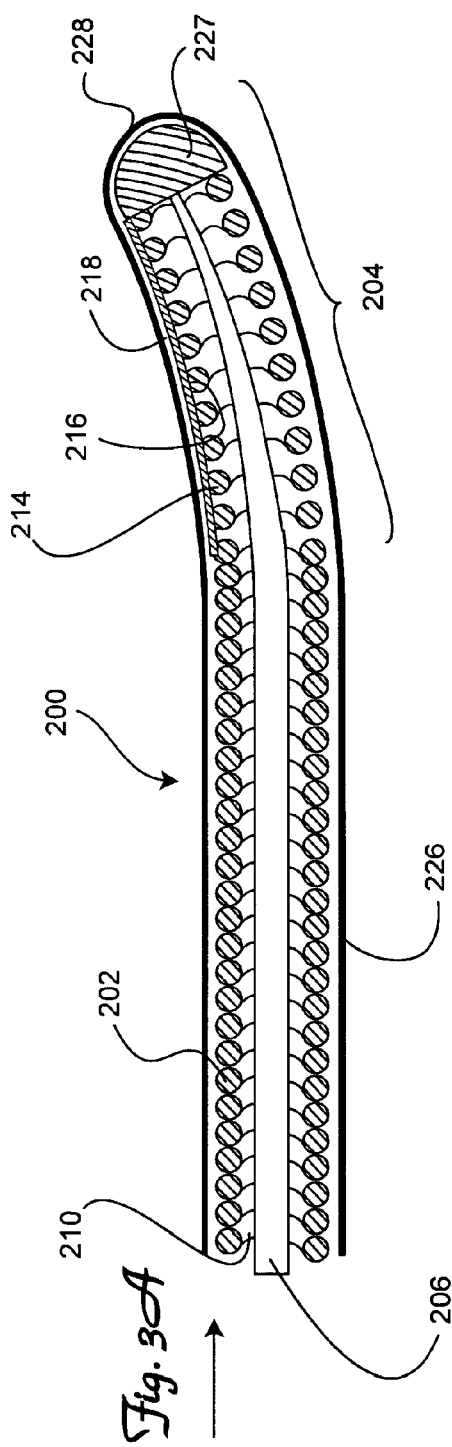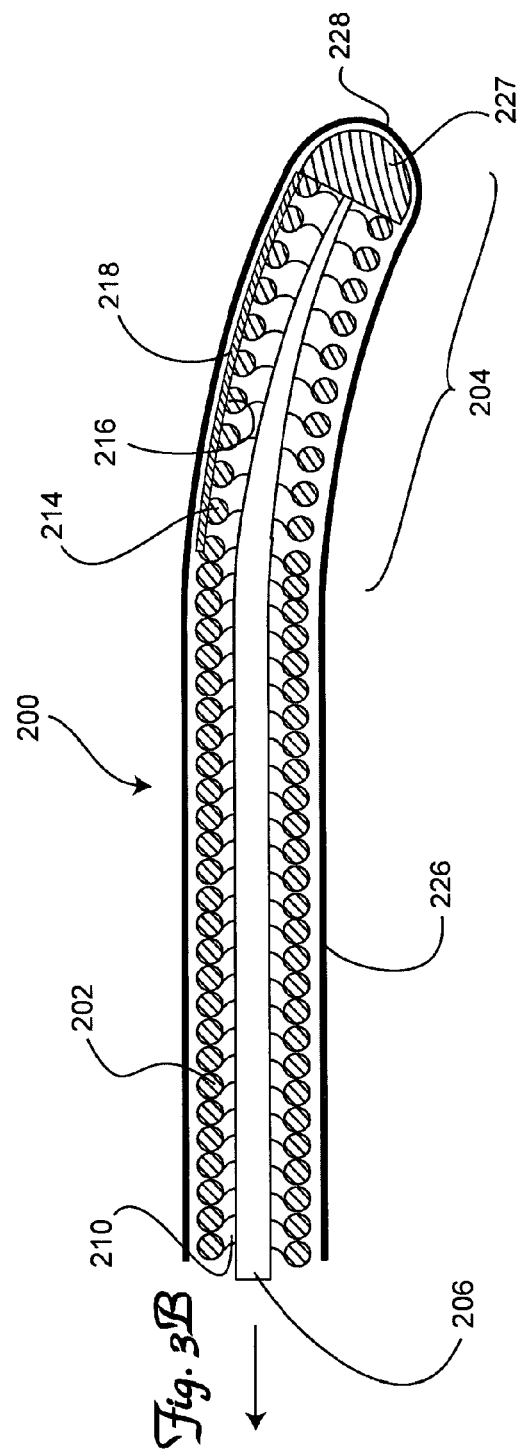

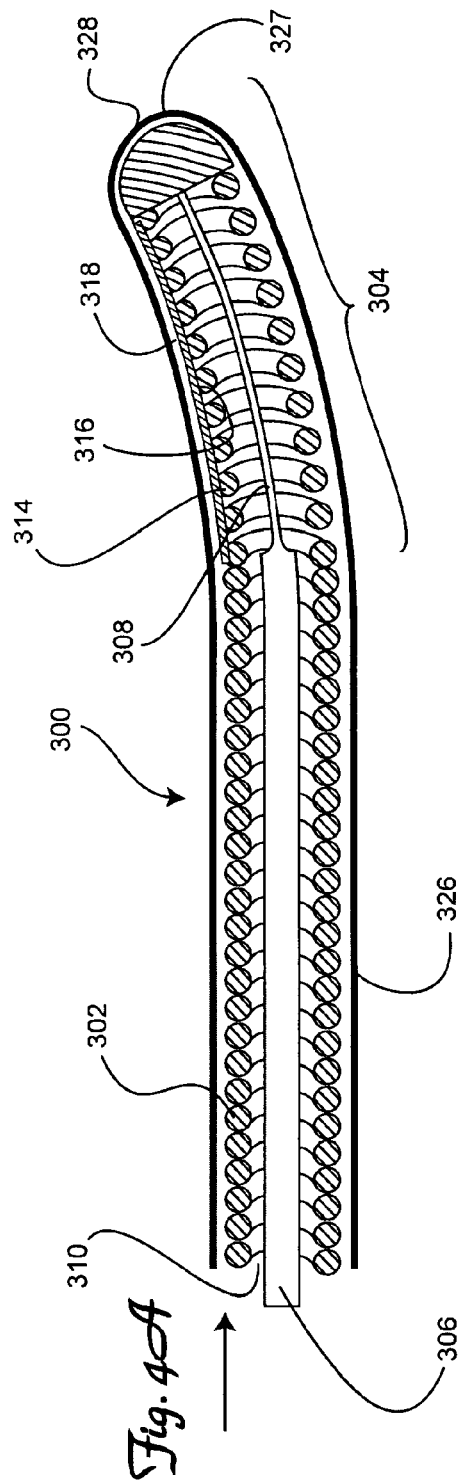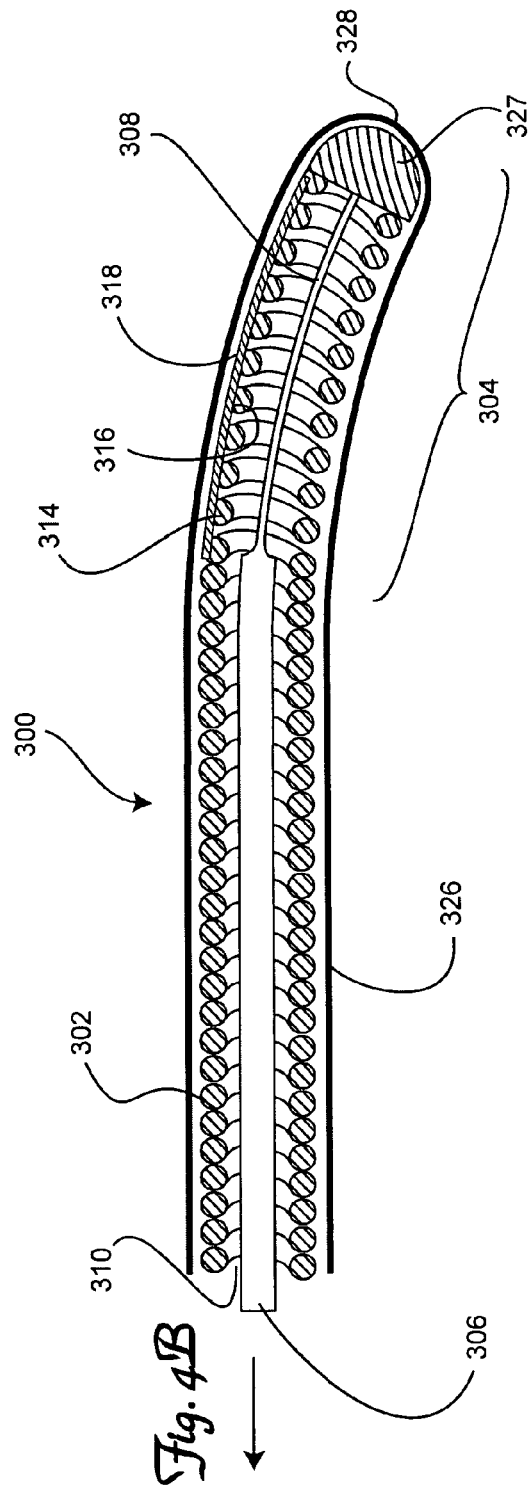

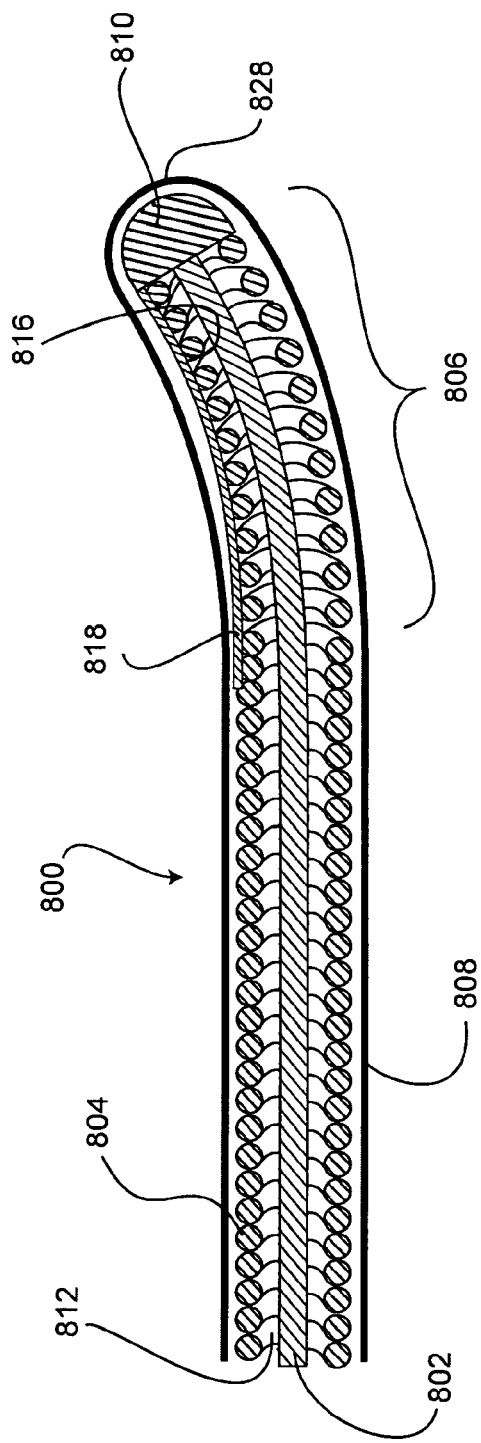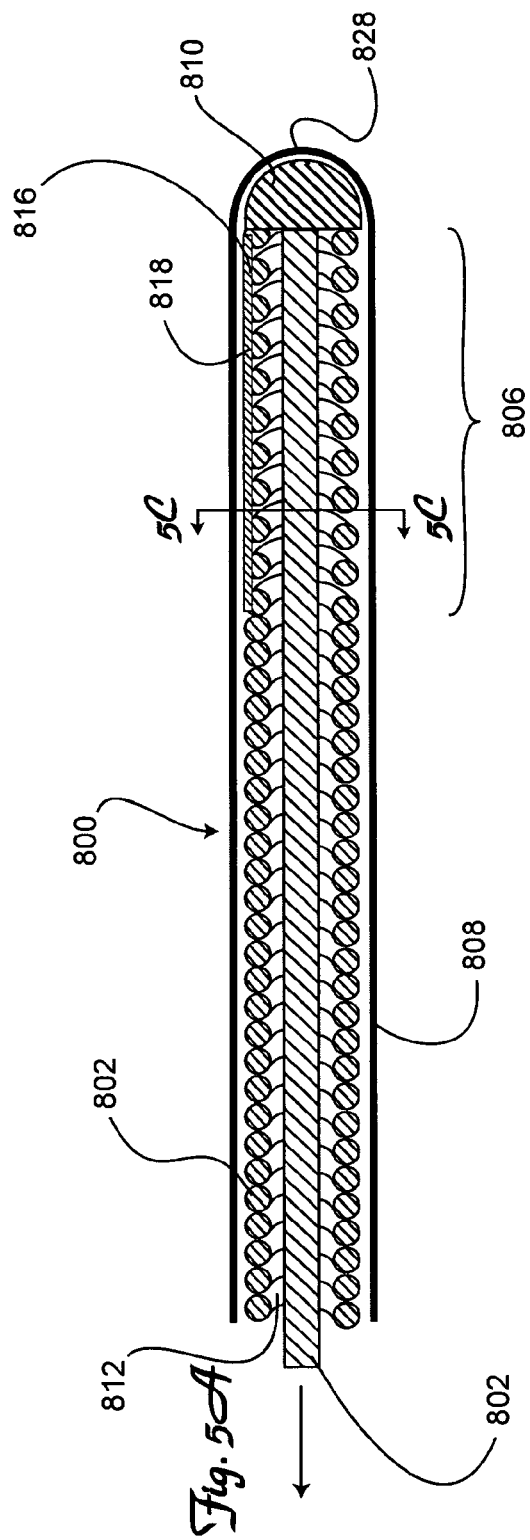

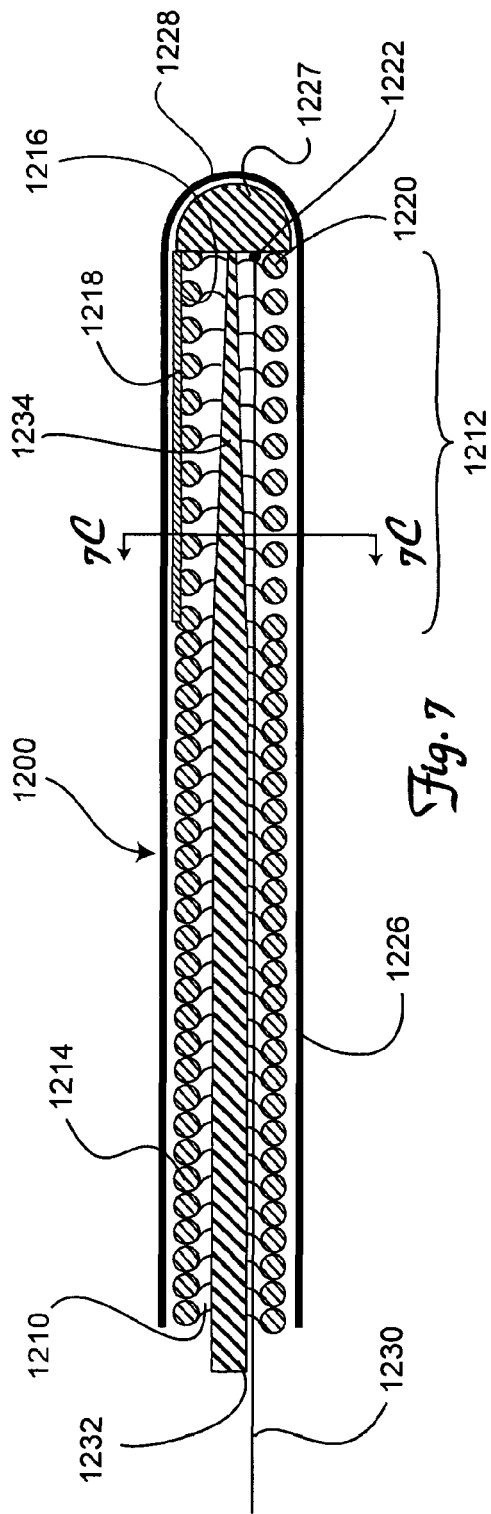
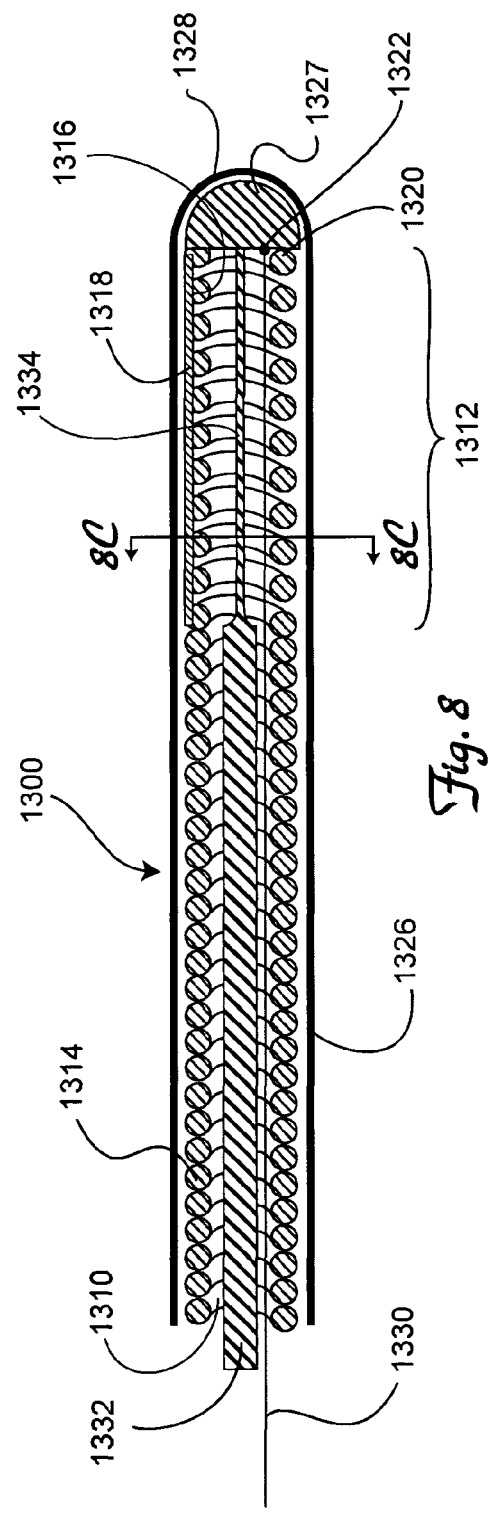

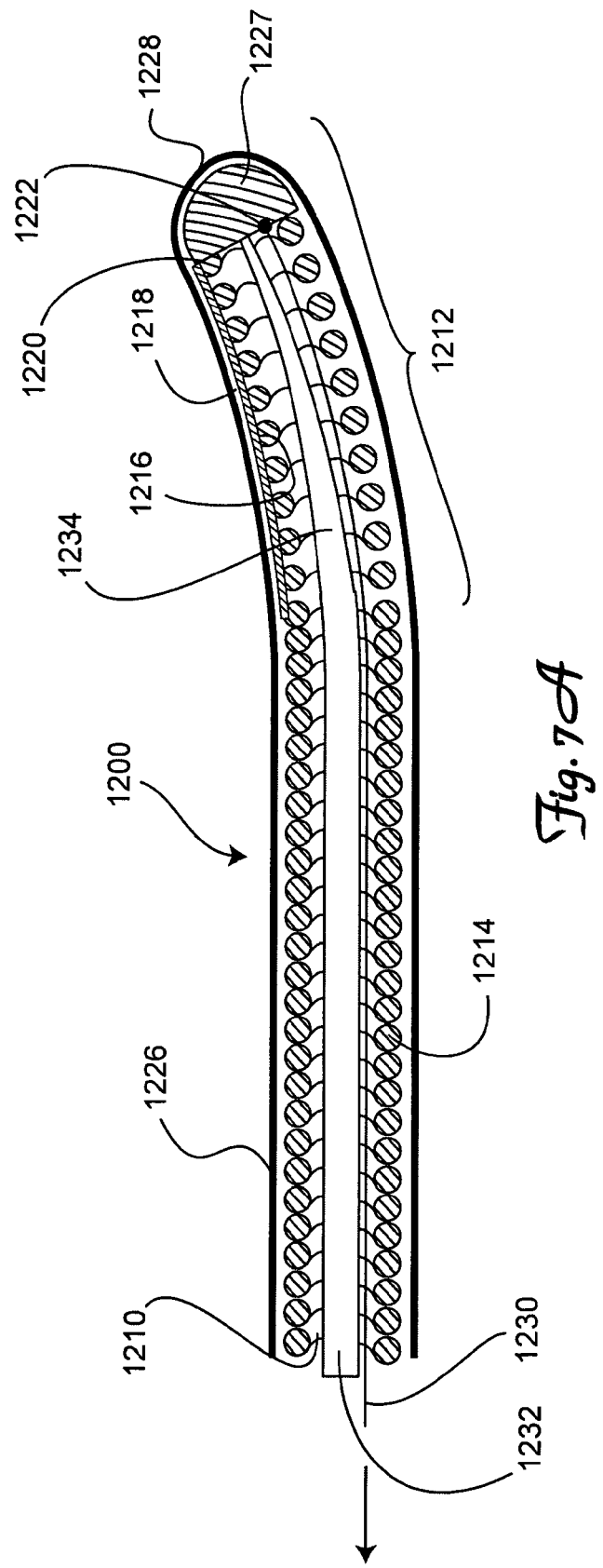

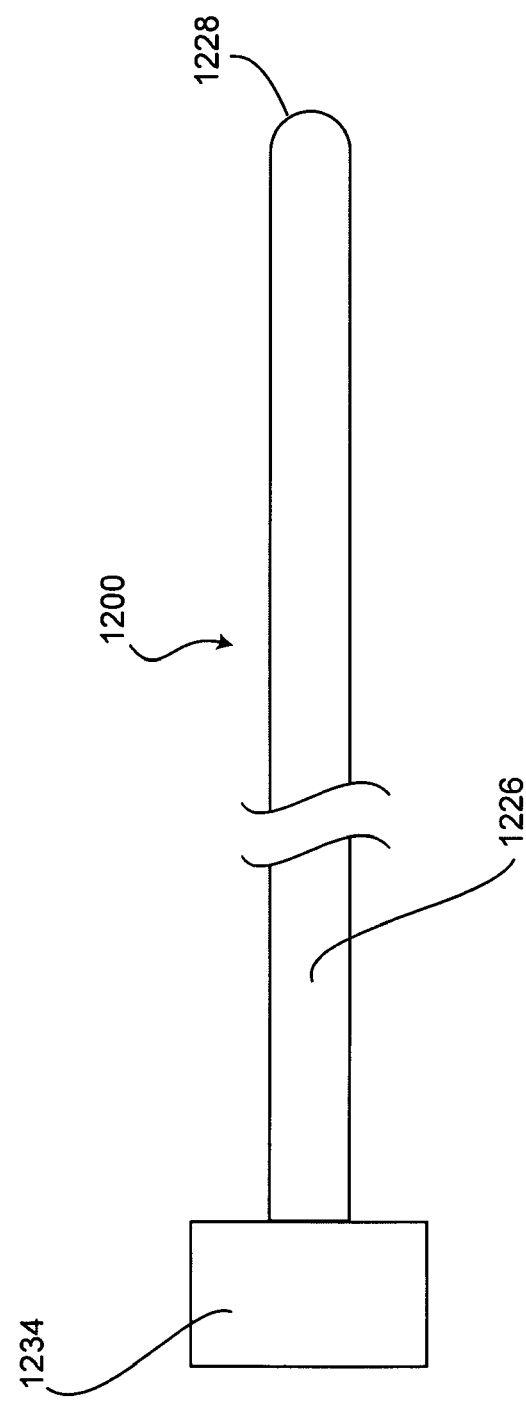

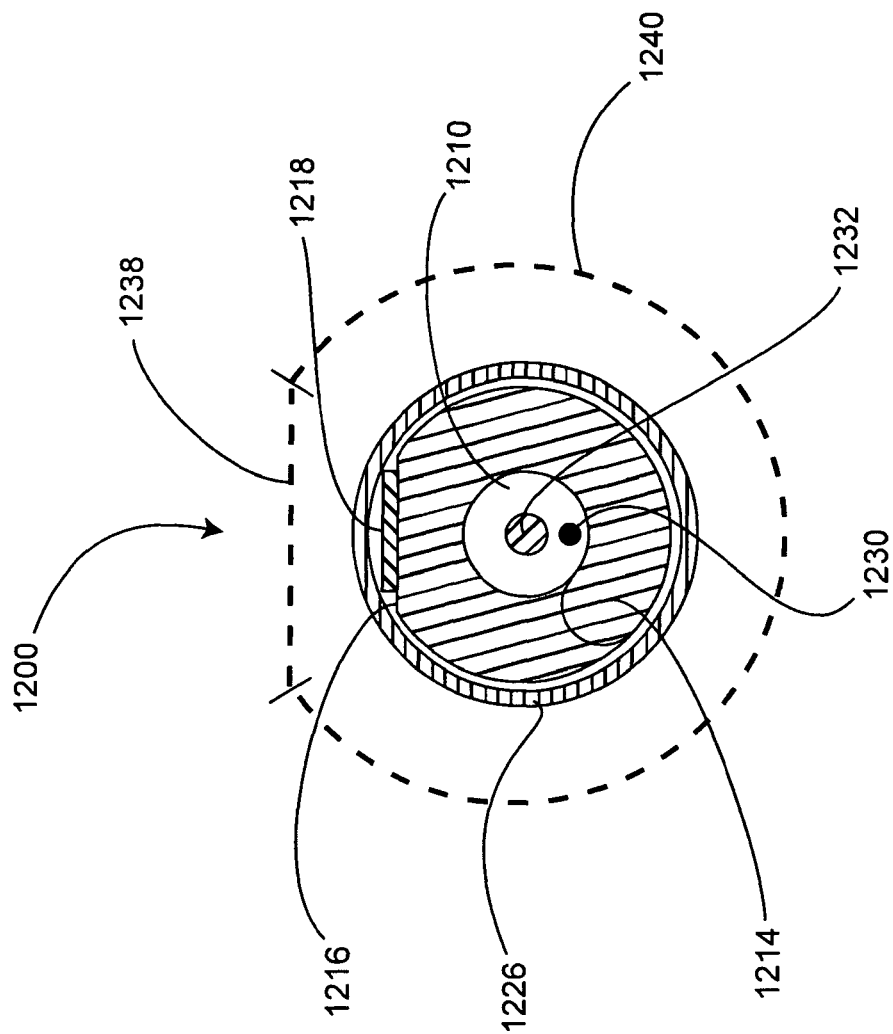

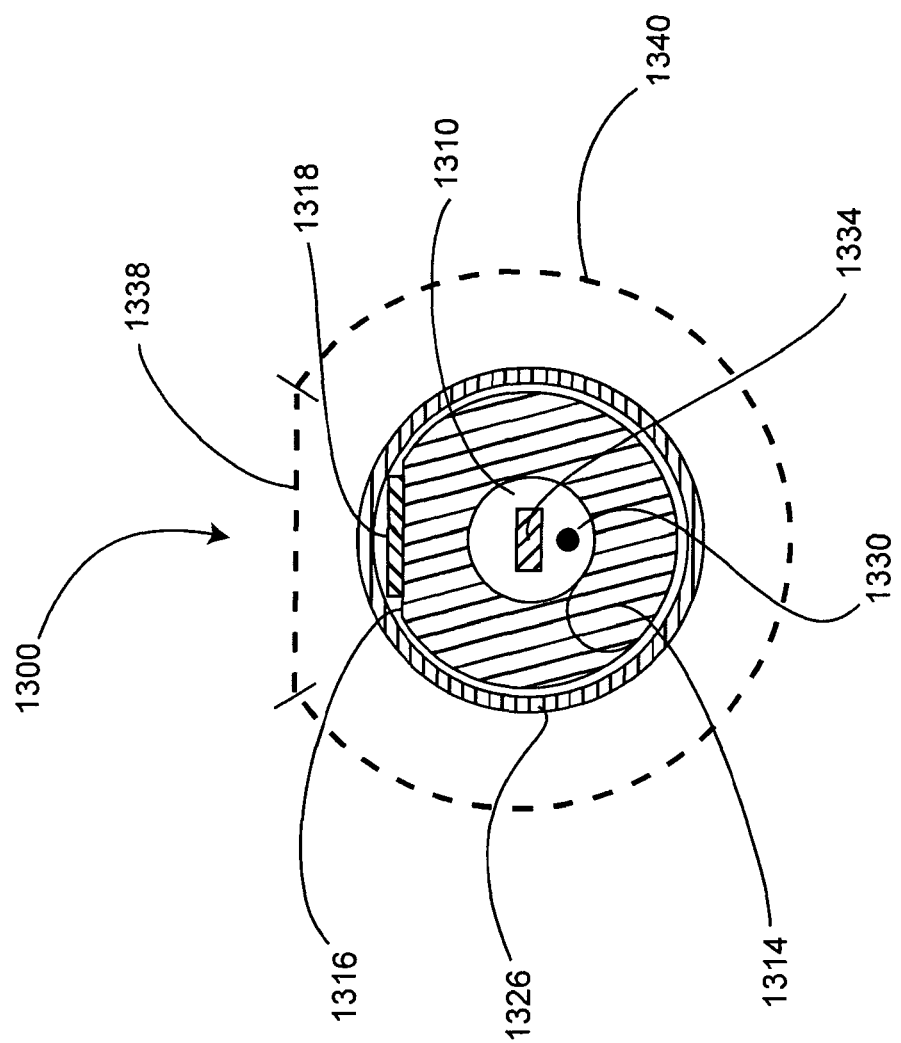

GUIDEWIRE

RELATED APPLICATION

This application is a continuation of U.S. application Ser. No. 12/321,882 filed Jan. 27, 2009 and titled GUIDEWIRE, the entire contents of which is incorporated herein by reference for all purposes.

FIELD OF THE INVENTION

The present invention relates to apparatus and methods for performing surgical or interventional procedures that access hollow conduits of mammalian anatomy. More particularly, the invention discloses devices for navigating tortuous vascular pathways, reaching and then crossing total occlusions in blood vessels and highly stenosed lesions.

BACKGROUND

Intracorporal medical devices have been developed and used to navigate and access the tortuous vascular anatomy and other hollow conduits of a mammalian body. Some of these devices include intravenous guidewires, stylets, intravenous catheters and related devices like endoscopes and colonoscopes that have a predetermined degree of flexibility and may have straight or pre-formed, shaped ends to guide the device through the anatomical conduit. Of the devices that are employed to reach vascular blockages, each has certain advantages and disadvantages. Many fall short of desired performance before reaching a vascular blockage because of a prolapse at a vascular bifurcation, an inability to enter a bifurcation or to be directed to the site of therapy. Others may reach an occlusion but then require a different device to be introduced before crossing the stenosis. The medical industry has striven to reach a balance between the flexibility required to negotiate around tortuous pathways and the rigidity necessary to stabilize a catheter's advancement. Many intravenous interventional guidewires provide directability, flexibility or stiffness but fail to do all or a combination at the same time. These products typically have pre-formed flexible distal ends that provide minimal directability but not true directability, flexibility and stiffness combined, which would be the most useful advantage. Additionally, most physicians must use a series of different diameter guidewires to perform one procedure, creating a procedure that costs additional time, money and risks patient safety from vascular injury.

Accessing occlusions having relatively sharp angles and passage constrictions using conventional guidewires having pre-formed "J" shapes or angled distal ends requires rotating the guidewire while simultaneously moving it proximally and distally. This action can cause damage to the fragile endothelial cell layer lining blood vessels. Additionally, conventional guidewires can lose their ability to be rotated when the flexible distal ends enter vessels of reduced diameter. Rotation of the guidewire following inserting the distal end into a vessel having a reduced diameter may produce relatively high frictional forces between the walls of the small vessels and the guidewire. A desirable device would therefore require reduced rotation and increased ability to advance in a forward or distal direction through tortuous anatomies.

Another undesirable characteristic of conventional guidewires is the inability to support a catheter at the flexible, tapered, distal end. When a catheter is advanced over a guidewire toward a vascular location in and close to a bifurcation, the catheter tends to proceed in a straight line rather than following the guidewire. Further, the natural pulsation of the vascular system of a living animal can cause a conventional guidewire to move within the body and thereby lose its distal location. To address the undesirable characteristic of a conventional guidewire that allows a catheter to prolapse, a guidewire that is stiffer on the distal end yet still able to be directed into a vascular bifurcation would prevent the catheter from proceeding in a straight line. It would also allow a stiffer catheter or a catheter with a larger diameter to be used.

Physicians generally have four objectives when using such vascular devices: (1) To reach the occlusion; (2) To reach the occlusion without causing vascular damage; (3) To cross the occlusion once it is reached; and (4) To reach the occlusion and cross it in as little time as possible. A device able to accomplish all four objectives would be extremely advantageous. It is not uncommon for a physician to place a catheter somewhere in a vessel and exchange the first guidewire with one or more secondary guidewires having progressively stiffer distal ends to prevent prolapse of the devices placed over the guidewire(s). These four objectives would be resolved by a guidewire stiff enough to be advanced through the vasculature and yet be directed into branched vessels with minimal rotational torque and minimal sliding back and forth in proximal and distal directions to enter a bifurcation. Yet another advantage would be having a guidewire stiff enough to be pushed and yet be directed into branched vessels with minimal torquing.

Vascular occlusions defined as Chronic Total Occlusions are blockages that can occur anywhere in a patient's vascular system, including coronary, carotid, renal, iliac, femoral, cerebral, popliteal and other peripheral arteries.

U.S. Pat. No. 4,676,249 to Arenas et al. discloses a guidewire having a moving internal member to provide stiffness when required, but does not disclose a directable distal end or the ability to cross occlusions. Another, U.S. Pat. No. 5,542,434 to Imran et al., discloses a longitudinally movable core wire made of a memory metal alloy that stiffens when subjected to thermal energy. Yet another, U.S. Pat. No. 5,605,162 to Mirzaee et al., uses a pull wire to draw the distal coil proximally to stiffen the distal end. These devices allow the wire to become stiff and yet torquable when desired, but fail when a catheter needs to be slid over the device. Both devices are deficient when they reach an occlusion with heavily calcified plaque in that they do not have sufficient stiffness to cross the occlusion.

For all these and other reasons there is a clear need for a guidewire that can vary the shape of its distal end, is relatively stiff and also has the ability to cross an occlusion.

SUMMARY

In one aspect, the guidewire of the present invention includes a shaft which defines a substantially circular lateral dimension, a length, a proximal section and a distal section having greater flexibility than the proximal section. The distal section defines a weak side and a strong side. An actuating member is attached to the distal section proximate a distal end of the distal section and is capable of transmitting longitudinal force to the distal section. When longitudinal force is applied to the actuating member, the weak side of the distal section changes size while the strong side maintains substantially the same size, resulting in the distal section deflecting.

In another aspect the guidewire of the present invention includes a shaft which defines a substantially circular lateral dimension, a length, a proximal section and a distal section having greater flexibility than the proximal section. The distal section of the shaft is a coil defining a first central space and an expandable side and a non-expandable side. A proximal section made of a hollow member defines a second central space substantially coaxial with the first central space. An actuating member extends through the first central space and the second central space and the actuating member is attached proximate a distal end of the distal section and is capable of transferring longitudinal force to the coil. Thus, when longitudinal force is applied to the actuating member, the expandable side of the distal section expands while the unexpandable side is prevented from expanding, resulting the distal section deflecting.

In an alternative aspect, the guidewire includes a coil which defines a length, a central space, a proximal section and a distal section, with the distal section further defining a distal end. An actuating member extends through the central space and is attached proximate the distal end of the coil and is capable of transferring longitudinal force to the coil. A side of the coil winds along the distal section is physically connected to define a non-expandable side on the connected side and an expandable side on the side where the coil winds are not connected. When longitudinal force is applied by the actuating member, the expandable side of the coil winds expands, resulting in the distal section assuming a deflected configuration having a different shape than the guidewire in a non-deflected configuration.

BRIEF DESCRIPTION OF THE DRAWINGS

FIG. 1 is a cross sectional centerline view taken along the longitudinal axis of a guidewire of the present invention.

FIG. 1A is a cross sectional centerline view taken along the longitudinal axis of the guidewire shown in FIG. 1, following the application of distal force, in a deflected configuration.

FIG. 1B is a cross sectional centerline view taken along the longitudinal axis of the guidewire shown in FIG. 1, following the application of proximal force, in a deflected configuration.

FIG. 1C is a broken side view of the guidewire shown in FIG. 1.

FIG. 2A is a cross sectional centerline view taken along the longitudinal axis of the guidewire shown in FIG. 2, following the application of distal force, in a deflected configuration.

FIG. 2B is a cross sectional centerline view taken along the longitudinal axis of the guidewire shown in FIG. 2, following the application of proximal force, in a deflected configuration.

FIG. 2D is a lateral cross section of the guidewire shown in FIG. 2 taken through the lines 2D-2D.

FIG. 3 is a cross sectional centerline view taken along the longitudinal axis of a guidewire of the present invention having an open wound distal coil and a distally tapered actuating member.

FIG. 3A is a cross sectional centerline view taken along the longitudinal axis of the guidewire shown in FIG. 3, following the application of distal force, in a deflected configuration.

FIG. 3B is a cross sectional centerline view taken along the longitudinal axis of the guidewire shown in FIG. 3, following the application of proximal force, in a deflected configuration.

FIG. 4 is a cross sectional centerline view taken along the longitudinal axis of a guidewire of the present invention having an open wound distal coil and a distally flattened actuating member.

FIG. 4A is a cross sectional centerline view taken along the longitudinal axis of the guidewire shown in FIG. 4, following the application of distal force, in a deflected configuration.

FIG. 4B is a cross sectional centerline view taken along the longitudinal axis of the guidewire shown in FIG. 4, following the application of proximal force, in a deflected configuration.

FIG. 5 is a cross sectional centerline view taken along the longitudinal axis of a guidewire of the present invention having a preformed distal end in the curved, unstressed configuration.

FIG. 5A is a cross sectional centerline view taken along the longitudinal axis of a guidewire of the present invention in the straightened, stressed configuration following the application of proximal force to the actuating member.

FIG. 7 is a cross sectional centerline view taken along the longitudinal axis of a guidewire of the present invention having an actuating mechanism attached to a distal end enabling the guidewire to deflect following the application of proximal force to the actuating member.

FIG. 7A is a cross sectional centerline view taken along the longitudinal axis of the guidewire shown in FIG. 7, following the application of proximal force, in a deflected configuration.

FIG. 7B is a broken side view of the guidewire shown in FIG. 7.

FIG. 7C is a cross section of the guidewire shown in FIG. 7 taken through the lines 7C-7C.

FIG. 8 is a cross sectional centerline view taken along the longitudinal axis of a guidewire of the present invention having an actuating mechanism attached to a distal end enabling the guidewire to deflect following the application of proximal force to the actuating member.

FIG. 8C is a cross section of the guidewire shown in FIG. 8 taken through the lines 8C-8C.

DETAILED DESCRIPTION

Nomenclature

Figure 1D:
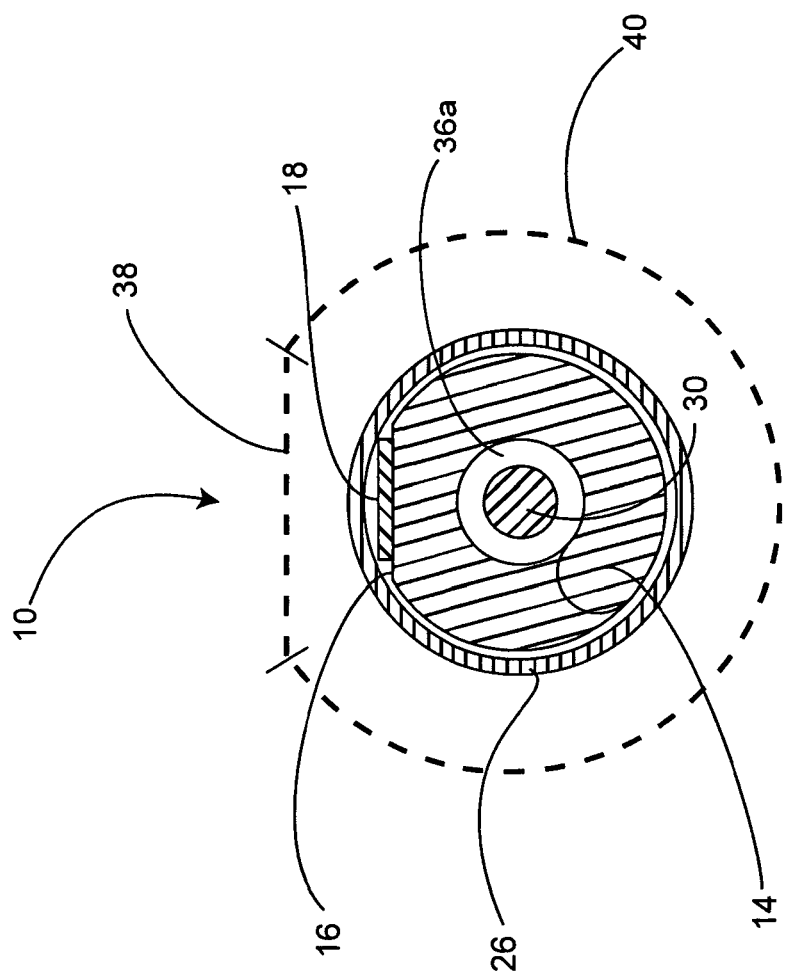
FIG. 1D is a lateral cross section of the guidewire shown in FIG. 1 taken through the lines 1D-1D.

10 Guidewire
12 Distal Section
14 Coil
16 Flattened Section of Coil
18 Ribbon
20 Distal End of Coil
22 Proximal End of Coil
23 Solder
24 Hollow Shaft
26 Coating
27 End Piece
28 Distal End of Guidewire
30 Actuating Member
32 Proximal Section
34 Handle
36a First Central Space (Coil)
36b Second Central Space (Hollow Shaft)
38 Non-Expandable Side
40 Expandable Side
50 Catheter
100 Guidewire
102 Coil
104 Distal Section
106 Proximal Section
110 Central Space
114 Open Wound Coil Section
116 Flattened Section of Coil
118 Ribbon
126 Coating
127 End Piece
128 Distal End of Guidewire
130 Actuating Member
134 Handle
138 Non-Expandable Side
140 Expandable Side
200 Guidewire
202 Coil
204 Distal Section
206 Actuating Member
208 Tapered Section of Actuating Member
210 Central Space
214 Open Wound Section of Coil
216 Flattened Section of Coil
218 Ribbon
226 Coating
227 End Piece
228 Distal End of Guidewire
234 Handle
238 Non-Expandable Side
240 Expandable Side
300 Guidewire
302 Coil
304 Distal Section
306 Actuating Member
308 Flat Section of Actuating Member
310 Central Space
314 Open Wound Section of Coil
316 Flattened Section of Coil
318 Ribbon
326 Coating
327 End Piece
328 Distal End of Guidewire
334 Handle
338 Non-Expandable Side
340 Expandable Side
800 Guidewire
802 Actuating Member
804 Coil
806 Distal Section
808 Coating
810 End Piece
812 Central Space
816 Flattened Section of Coil
818 Ribbon
828 Distal End of Guidewire
834 Handle
838 Non-Expandable Side
840 Expandable Side
1100 Guidewire
1110 Central Coil Space
1112 Distal Section
1114 Coil
1116 Flattened Section of Coil
1118 Ribbon
1120 Distal End of Coil
1122 Actuating Member Attachment
1126 Coating
1127 End Piece
1128 Distal End of Guidewire
1130 Actuating Member
1132 Core Wire
1134 Handle
1138 Non-Expandable Side
1140 Expandable Side
1200 Guidewire
1210 Central Space
1212 Distal Section
1214 Coil
1216 Flattened Section of Coil
1218 Ribbon
1220 Distal End of Coil
1222 Actuating Member Attachment
1226 Coating
1227 End Piece
1228 Distal End of Guidewire
1230 Actuating Member
1232 Core Wire
1234 Tapered Section of Core Wire
1236 Handle
1238 Non-Expandable Side
1240 Expandable Side
1300 Guidewire
1310 Central Space
1312 Distal Section
1314 Coil
1316 Flattened Section of Coil
1318 Ribbon
1320 Distal End of Coil
1322 Actuating Member Attachment
1326 Coating
1327 End Piece
1328 Distal End of Guidewire
1330 Actuating Member
1332 Core Wire
1334 Flattened Section of Core Wire
1336 Handle
1338 Non-Expandable Side
1340 Expandable Side

DEFINITIONS

"Anatomical Conduit" refers to a naturally occurring vessel or duct within a patient's body.

"Distal" means further from the operator (e.g., physician or technician) of a device.

"Distal Force" means force applied in a distal direction or toward a distal end of the device.

"Handle" means a device used to grip certain components of the invention for the purpose of causing longitudinal movement of additional components.

"Longitudinal Force" means either distal force or proximal force.

"Prolapse" refers to an adverse event when a medical device does not follow the desired path at a vascular bifurcation but instead where a relatively stiff device forces a relatively less stiff device straight through the vessel, pulling the less stiff device out of the side branch of the bifurcation.

"Proximal" means closer to the operator (e.g., physician or technician) of a device.

"Proximal Force" means force applied in a proximal direction or toward a proximal end of the device.

CONSTRUCTION

The following detailed description is to be read with reference to the drawings in which similar components in different drawings have the same nomenclature. The drawings, which are not necessarily to scale, show illustrative embodiments and are not intended to limit the scope of the invention.

It should be noted that combinations of materials and components described within this specification may be interchangeable and anyone skilled in the art will understand that a combination of materials or exchange of other materials to accomplish the work of the invention will not depart from the spirit of the invention. It is further understood that the invention is not limited to vascular use and can also be applied to use through an endoscope, gastroenterological procedures, laparoscope, artherectomy procedures, urological procedures or neurological procedures.

For the purpose of describing the actuation of all embodiments of the invention as described below, a generic handle 34, 134, 234, 334, 834, 1134, 1236, 1336 is used. The function of the handle 34, 134, 234, 334, 834, 1134, 1236, 1336 is to grip the outermost hollow shaft 24 or coated coil 102, 202, 302, 804, 1114, 1214, 1314 and move the actuating member 30, 130, 206, 306, 802, 1130, 1230, 1330. Using the handle 34, 134, 234, 334, 834, 1134, 1236, 1336 allows application of longitudinal force from the proximal end to the actuating member 30, 130, 206, 306, 802, 1130, 1230, 1330 and proximal force to the actuating member 1130, 1230, 1330, which causes the distal section 12, 104, 204, 304, 806, 1112, 1212, 1312 to deflect. As described in detail below, the application of distal or proximal force causes the distal section 12, 104, 204, 304 of the guidewire 10, 100, 200, 300 to deflect back toward the proximal end (not shown). Applying distal force to the guidewire 800, which is trained to be deflected in an unstressed configuration, causes the distal section 806 to straighten. The embodiments of the guidewire 1100, 1200, 1300 deflect when proximal force is applied via the actuating member 1130, 1230, 1330.

FIGS. 1-1B show a longitudinal cross sectional centerline view of an embodiment of the guidewire 10. The guidewire 10 includes a distal section 12, which as described below, can be used for a number of purposes, primarily steerability. An actuating member 30 extends substantially the length of the guidewire 10 and is proximally connected to a handle 34 as shown in FIG. 1C which allows longitudinal and rotational control by an operator and is distally attached to a hemispherical end piece 27. As shown in FIGS. 1-1B, the end piece 27 is integrally attached to the actuating member 30, but may also be a separate, attached structure (not shown). The actuating member 30 can be made from a variety of materials having sufficient strength to be able to cause the distal section 12 to deflect and still be flexible enough to curve with the coil 14 including but not limited to stainless steel alloys, nickel titanium alloys and reinforced polymeric materials such as Kevlar® or fabric materials. The coil 14 defines a distal end 20, a proximal end 22 and a first central space 36a through which a distal section (unnumbered) of the actuating member 30 extends and ends proximally of the hemispherical end piece 27. In one embodiment, the coil 14 can be made from a radiopaque material such as a platinum-nickel alloy that allows the physician to visualize the position of the coil 14 using radiological means, thereby navigating the guidewire 10 into desired anatomical pathways with minimal forward motion. A ribbon 18 is fixedly attached to, and at least partially resides in, a flattened section 16 configured into an outer surface (unnumbered) of the coil 14 and functions to bind together the portions of the coil 14 to which it is attached, creating a non-expandable (or strong) side 38 and an expandable (or weak) side 40. Means of attaching the ribbon 18 to the flattened section 16 include but are not limited to adhesives, laser welding, or soldering. The ribbon 18 is made of a suitable metallic material such as an austenitic stainless steel alloy or tungsten alloy, such as tungsten-molybdenum and tungsten-rhenium. In some instances iridium is added to the alloy, to increase strength and radiopaqueness. In another embodiment (not shown) the ribbon 18 is not used and instead the non-expandable side 38 of the distal section 12 is defined by a series of welds (not shown), gluing (not shown) or mechanical fasteners (not shown) affixed to the coil winds. In an alternative embodiment (not shown), the ribbon 18 is replaced by application of a polymer fused to coil 14 to include a polymer fiber. The fiber (not shown) is entangled into coil 14 by means of weaving in and out of the coil 14 winds and looping around the individual coil winds to form a solid attachment after application of an adhesive. In yet another embodiment (not shown) the ribbon 18 comprises a length of high strength adhesive tape affixed to the flattened section 16.

At its proximal end 22 the coil 14 is attached to a hollow shaft 24 by solder 23, welding (not shown), gluing (not shown), mechanical fastener (not shown) or another method (not shown). The hollow shaft 24 defines a second central space 36b and extends distally from the handle 34 to the proximal end 22 of the coil 14 and surrounds the actuating member 30 up to the point where the coil 14 is attached by solder 23. Materials the hollow shaft 24 can be made from include, but are not limited to stainless steel and nickel-titanium alloy hypotube as well as polymer hollow shaft materials such as PEEK, urethanes, polycarbonate materials and fiber reinforced polyimide materials. The hollow member 24 functions to stiffen the guidewire 10 up to the point of coil 14 attachment. A coating 26 such as non-thrombogenic polymers, PTFE, ePTFE, FEP, polyester, polyurethane, polyethylene, silicone or hydrophilic may be applied over the coil 14 and hemispherical end piece 27 to improve sterility as well as enhancing the outer smoothness of the guidewire 10, thereby causing less trauma to the patient during introduction, the procedure itself and removal. In one embodiment the coating 26 is applied to the coil 14 and hollow shaft 24 by applying a polymer heat shrink tubing such as a PTFE, FEP, or polyester, followed by the application of a proper amount of heat or an appropriate length of time. In additional embodiments the coating 26 is applied by dipping the guidewire 10 into a dispersion polymer such as urethane or silicone, by spraying a polymer such as PTFE, FEP, polyester or silicone or by a co-extrusion process of a polymer such as PTFE, FEP, polyester, urethane or silicone. An additional advantage of a coating 26 is a reduction in adverse reactions due to repulsion of platelets, proteins, cells or other fouling materials, which can cause fibrin clot production. FIG. 1C is a broken side view of the entire guidewire 10, showing placement of a handle 34 on the proximal end (unnumbered). FIG. 1D is a lateral cross section of the guidewire 10 taken through the lines 1D-1D and illustrates the locations of the non-expandable side 38 and expandable side 40.

When distal force is applied to the actuating member 30 by the operator, as shown in FIG. 1A, the distal section 12 deflects due to the non-expandable side 38 to which the ribbon 18 is attached being prevented from expanding while allowing the expandable side 40 to expand, resulting in the distal section 12 assuming a deflected configuration as best shown in FIG. 1A. As shown in FIG. 1B, if proximal force is applied to the actuating member 30 the distal section 12 is deflected in the opposite direction as when distal force is applied. This is due to the pitch of the coil 14 having a relatively loose or open pitch to the coil winds (unnumbered), which allows the coil winds (unnumbered) on the expandable side 40, to be forced into a closer configuration. If the actuating member 30 is coupled with an actuating mechanism (not shown) such as a vernier type mechanism (not shown) a predictable and variable amount of deflection can be achieved with the application of a given amount of longitudinal force.

Figure 2:
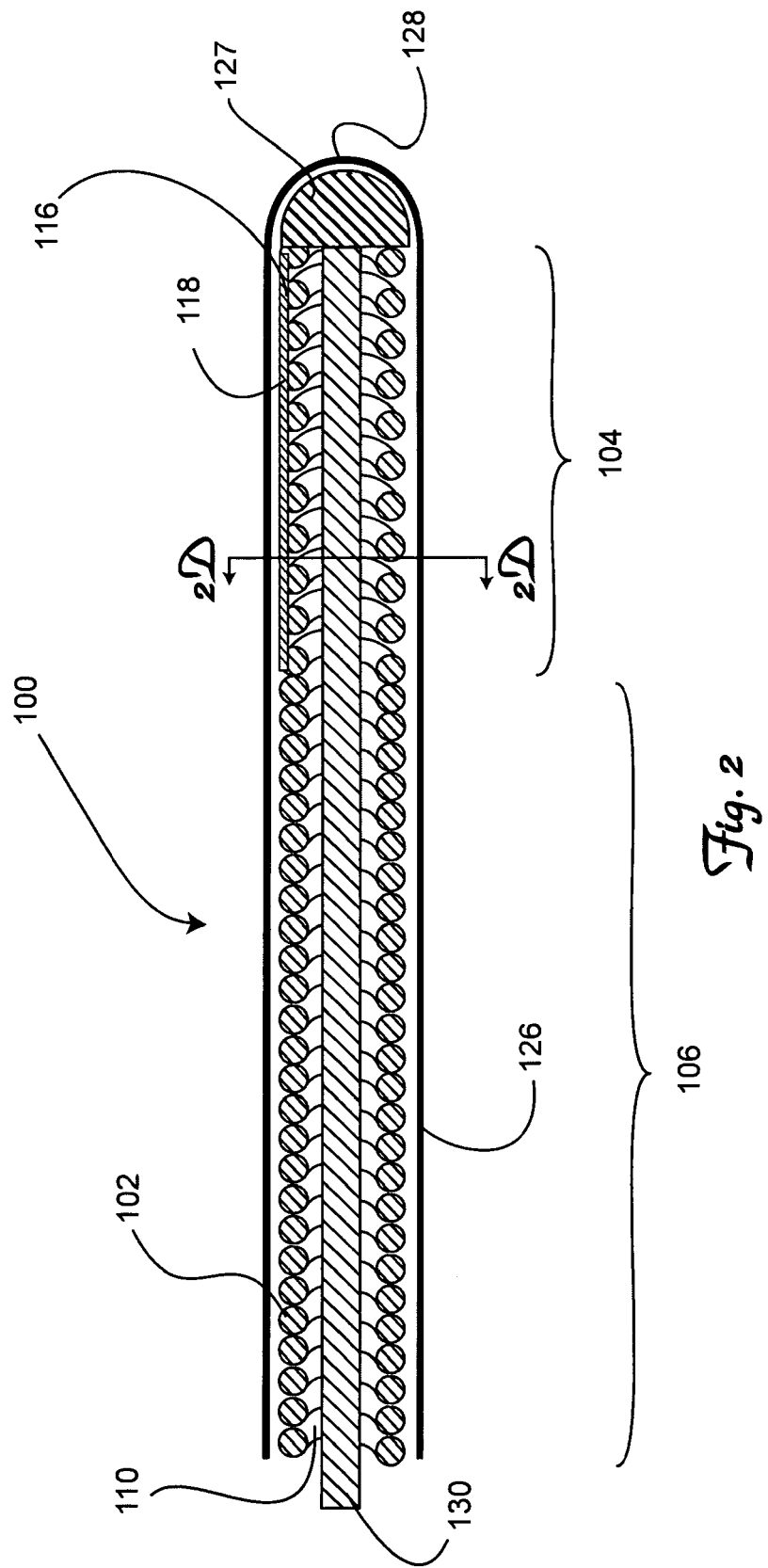
FIG. 2 is a cross sectional centerline view taken along the longitudinal axis of a guidewire of the present invention having a closed wound coil extending from the proximal device end to the proximal end of the distal section and an open wound coil on the distal section.

FIGS. 2-2B show a longitudinal cross sectional view of an alternative embodiment of the invention. A guidewire 100 is similar to the guidewire 10 as shown in FIGS. 1-1D, with the difference being that the coil 102 extends proximally substantially the length of the guidewire 100. In this embodiment, the proximal section 106 of the coil 102 replaces the hollow member 24 of FIGS. 1-1C and functions to support the guidewire 100 while allowing a greater degree of proximal flexibility which may be needed for some procedures. An actuating member 130 extends the length of the guidewire 100 through a central space 110 defined inside the coil winds (unnumbered) and is proximally connected to a handle 134 which allows longitudinal control by an operator and is distally attached to a hemispherical end piece 127. As shown in FIG. 2, the end piece 127 is integrally attached to the actuating member 130, but may also be a separate, attached structure (not shown). The actuating member 130 can be made from a variety of materials having sufficient stiffness to be able to cause the coil 102 to deflect the distal section 104, including but not limited to stainless steel alloys, nickel titanium alloys and reinforced polymeric materials such as Kevlar® or fabric materials. In one embodiment, the coil 102 can be made from a radiopaque material such as a platinum-nickel alloy that allows the physician to visualize the position of the coil 102 thereby allowing precise navigation of the guidewire 100 into desired pathways with minimal forward motion. A distal section 104 is defined by the end piece 127 and a ribbon 118. It will be observed that the distal section 104 is also defined by the distal section of the coil 102 being less closely wound, or open wound than the proximal section 106 of the coil 102. The open wound coil section 114 functions to lessen and more precisely control the amount of distal force required to place the guidewire 100 into a deflected configuration as shown in FIGS. 2A-2B. The ribbon 118 is fixedly attached to, and at least partially resides in, a flattened section 116 configured into an outer surface (unnumbered) of the coil 114 and functions to bind together the portions of the coil 114 to which it is attached, creating a strong side (unnumbered) of the distal section, creating a non-expandable side 138 and an expandable side 140. Means of attaching the ribbon 118 to the flattened section 116 include but are not limited to adhesives, laser welding, or soldering. The ribbon 118 is made of a suitable metallic material such as an austenitic stainless steel alloy or tungsten alloy, such as tungsten-molybdenum and tungsten-rhenium. In some instances iridium is added to the alloy, to increase strength and radiopaqueness. In another embodiment (not shown) the ribbon 118 is not used and instead the non-expandable side 138 is defined by a series of welds (not shown), gluing (not shown) or mechanical fasteners (not shown) affixed to the coil winds. In an alternative embodiment (not shown), the ribbon 118 is replaced by application of a polymer fused to coil 114 to include a polymer fiber. The fiber (not shown) is entangled into coil 114 by means of weaving in and out of the coil 114 winds and looping around the individual coil winds to form a solid attachment after application of an adhesive. In another embodiment (not shown) one side of the distal section 104 is bound together by a series of welds (not shown), gluing (not shown) or mechanical fasteners (not shown) affixed to the coil winds. In yet another embodiment (not shown) the ribbon 118 comprises a length of high strength adhesive tape affixed to the flattened section 116.

Figure 2C:
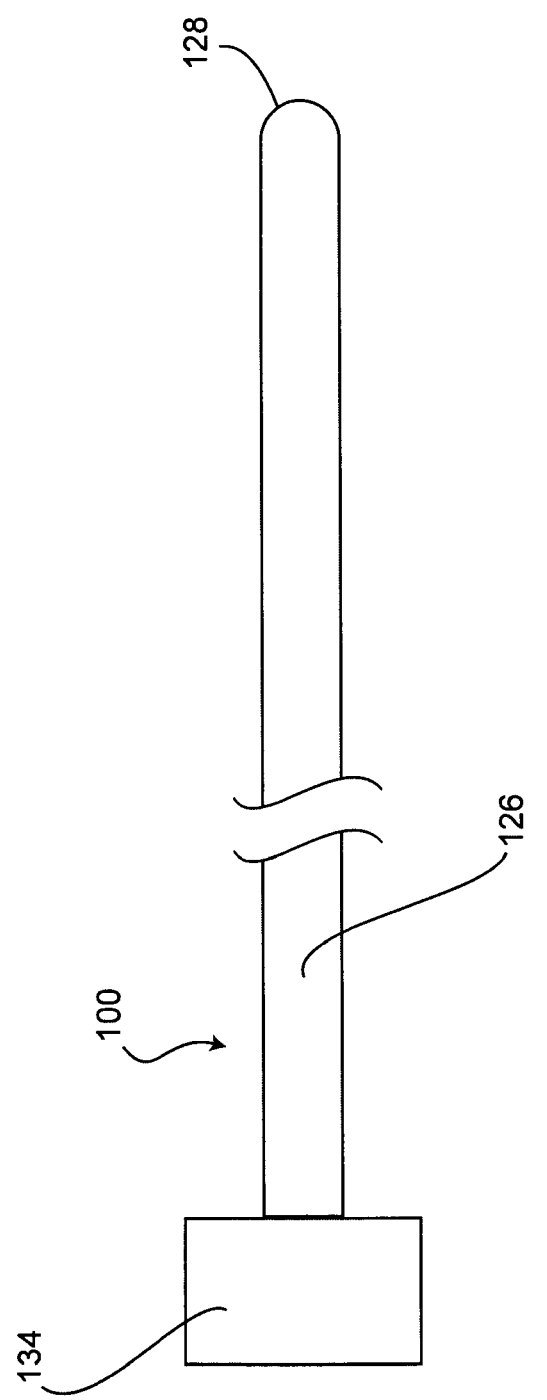
FIG. 2C is a broken side view of the guidewire shown in FIG. 2.

As shown in FIG. 2A, when distal force is applied to the actuating member 130 by the operator, the distal section 104 will deflect toward the proximal end (not shown), due to the non-expandable side 138, to which the ribbon 118 is attached, being unable to expand while allowing the expandable side 140 to expand, resulting in the distal section 104 assuming a deflected configuration. As shown in FIG. 2B, if proximal force is applied to the actuating member 130 the distal section 104 will deflect in the opposite direction as when distal force is applied. This is due to the pitch of the coil 102 corresponding with the distal section 104 having a relatively loose or open pitch to the coil winds (unnumbered), which allows the coil winds (unnumbered) on the expandable side 140 to be forced into a closer configuration. If the actuating member 130 is coupled with an actuating mechanism (not shown) such as a vernier type mechanism (not shown) a predictable and variable amount of deflection can be achieved with the application of a given amount of longitudinal force. A coating 126 such as non-thrombogenic polymers, PTFE, ePTFE, FEP, polyester, polyurethane, polyethylene, silicone or hydrophilic may be applied over the coil 102 and hemispherical end piece 127 to improve sterility as well as enhancing the outer smoothness of the guidewire 100, thereby causing less trauma to the patient during introduction, the procedure itself and removal. In one embodiment the coating 126 is applied to the coil 102 by applying a polymer heat shrink tubing such as a PTFE, FEP, or polyester, followed by the application of a proper amount of heat or an appropriate length of time. In additional embodiments the coating 126 is applied by dipping the guidewire 100 into a dispersion polymer such as urethane or silicone, by spraying a polymer such as PTFE, FEP, polyester or silicone or by a co-extrusion process of a polymer such as PTFE, FEP, polyester, urethane or silicone. An additional advantage of a coating 126 is a reduction in adverse reactions due to repulsion of platelets, proteins, cells or other fouling materials, which can cause fibrin clot production. FIG. 2C is a broken side view of the entire guidewire 100, showing placement of a handle 134 on the proximal end (unnumbered). FIG. 2D is a lateral cross section of the guidewire 100 taken through the lines 2D-2D illustrating the locations of the non-expandable side 138 and expandable side 140.

Figure 3C:
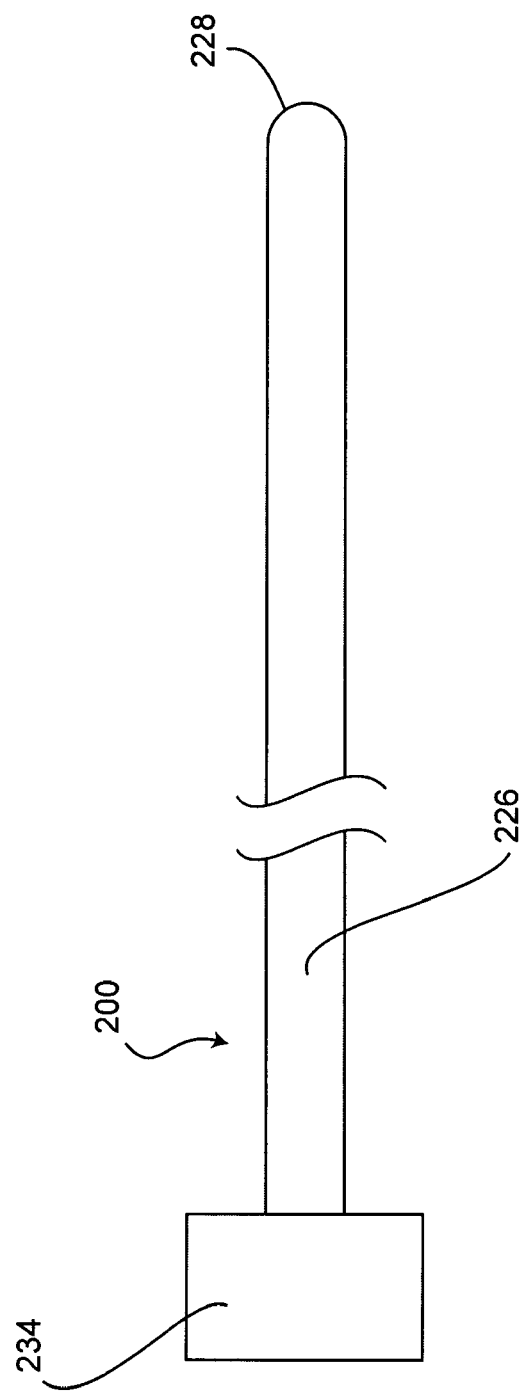
FIG. 3C is a broken side view of the guidewire shown in FIG. 3.

FIGS. 3-3B show a longitudinal cross sectional view of another embodiment of the invention. The guidewire 200 is similar to the guidewire 100 as shown in FIGS. 2-2A, with the difference being that an actuating member 206 further defines a tapered section 208 to further lessen and more precisely control the amount of longitudinal force required to place the guidewire 200 into a deflected configuration. A further advantage of a tapered section 208 of the actuating member 206 is that it will more readily deflect when striking an abrupt change in the patient's vasculature, thus being less likely to cause trauma. The actuating member 206 extends substantially the length of the guidewire 200 through a central space 210 defined inside the coil winds (unnumbered) and is proximally connected to a handle 234 (as shown in FIG. 3C) which allows control by an operator and is distally attached to a hemispherical end piece 227. As shown in FIGS. 3-3B, the end piece 227 is integrally attached to the actuating member 230, but may also be a separate, attached structure (not shown). The actuating member 206 can be made from a variety of materials having sufficient stiffness to be able to cause the distal section 204 to deflect and still be flexible enough to curve with the coil 202, including but not limited to stainless steel alloys, nickel titanium alloys and reinforced polymeric materials such as Kevlar® or fabric materials. In one embodiment, the coil 202 can be made from a radiopaque material such as a platinum-nickel alloy that allows the physician to visualize the position of the coil 202 thereby allowing precise navigation of the guidewire 200 into desired pathways with minimal rotational or reverse motion. A distal section 204 is defined by a ribbon 218 and the end piece 237. It will be observed that the distal section 204 is also defined by an open wound section 214 of the coil 202 which is less closely wound, or has a lesser pitch than a proximal section (unnumbered). The open wound coil section 214 functions to further lessen and more precisely control the amount of longitudinal force required to place the guidewire 200 into a deflected configuration (not shown). The ribbon 218 is fixedly attached to, and at least partially resides on, a flattened section 216 configured into an outer surface (unnumbered) of the coil 202 and functions to bind together the portions of the coil 202 to which it is attached. Means of attaching the ribbon 218 to the flattened section 216 include but are not limited to adhesives, laser welding, or soldering. The ribbon 218 is made of a suitable metallic material such as an austenitic stainless steel alloy or tungsten alloy, such as tungsten-molybdenum and tungsten-rhenium. In some instances iridium is added to the alloy, to increase strength and radiopaqueness. In another embodiment (not shown) the ribbon 218 is not used and instead the strong side (unnumbered) of the distal section 204 is defined by a series of welds (not shown), gluing (not shown) or mechanical fasteners (not shown) affixed to the coil winds. In an alternative embodiment (not shown), the ribbon 218 is replaced by application of a polymer fused to coil 202 to include a polymer fiber. The fiber (not shown) is entangled into coil 202 by means of weaving in and out of the coil 202 winds and looping around the individual coil winds to form a solid attachment after application of an adhesive. In another embodiment (not shown) the distal section 204 is defined by a series of welds (not shown), gluing (not shown) or mechanical fasteners (not shown) affixed to the coil winds. In yet another embodiment (not shown) the ribbon 218 comprises a length of high strength adhesive tape affixed to the flattened section 216.

Figure 3D:
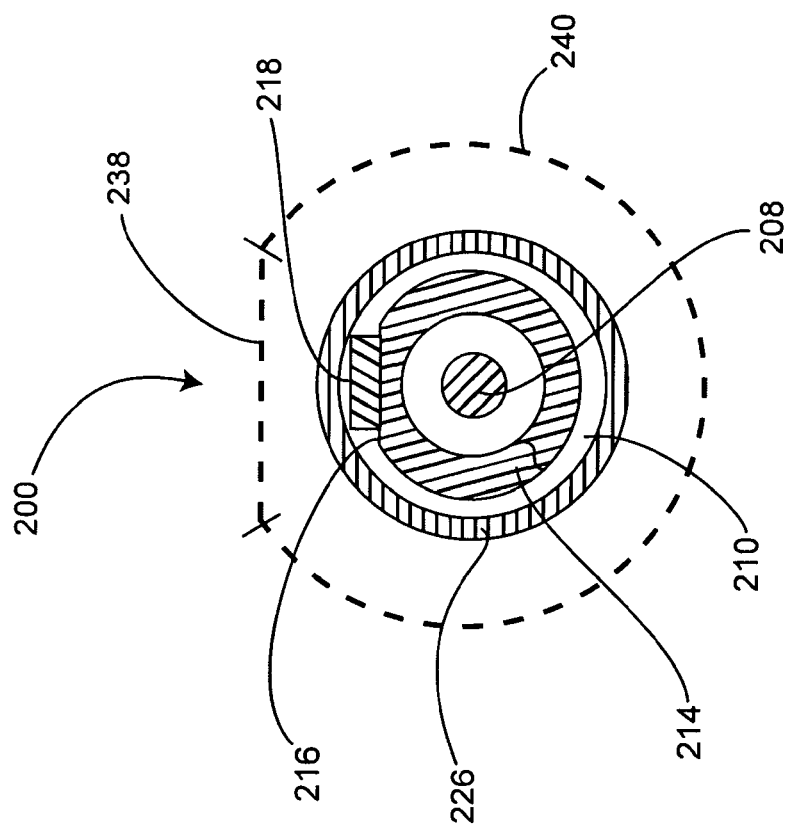
FIG. 3D is a cross section of the guidewire shown in FIG. 3 taken through the lines 3D-3D.

As shown in FIG. 3A, when distal force is applied to the actuating member 206 by the operator, the distal section 204 will deflect toward the proximal end (not shown), due to the non-expandable side 238 of the coil 202 to which the ribbon 218 is attached being unable to expand while allowing the expandable side 240 to expand, resulting in the distal section 204 assuming a deflected configuration. As shown in FIG. 3B, if proximal force is applied to the actuating member 206 the distal section 204 deflects in the opposite direction as when distal force is applied. This is due to the pitch of the coil 202 having a relatively loose or open pitch to the coil winds (unnumbered), which allows the coil winds (unnumbered) on the expandable side 240, to be forced into a closer configuration. If the actuating member 206 is coupled with an actuating mechanism (not shown) such as a vernier type mechanism (not shown) a predictable and variable amount of curvature can be achieved with the application of a given amount of distal force. A coating 226 such as non-thrombogenic polymers, PTFE, ePTFE, FEP, polyester, polyurethane, polyethylene, silicone or hydrophilic may be applied over the coil 202 and hemispherical end piece 227 to improve sterility as well as enhancing the outer smoothness of the guidewire 200, thereby causing less trauma to the patient during introduction, the procedure itself and removal. In one embodiment the coating 226 is applied to the coil 202 by applying a polymer heat shrink tubing such as a PTFE, FEP, or polyester, followed by the application of a proper amount of heat or an appropriate length of time. In additional embodiments the coating 226 is applied by dipping the guidewire 200 into a dispersion polymer such as urethane or silicone, by spraying a polymer such as PTFE, FEP, polyester or silicone or by a co-extrusion process of a polymer such as PTFE, FEP, polyester, urethane or silicone. An additional advantage of a coating 226 is a reduction in adverse reactions due to repulsion of platelets, proteins, cells or other fouling materials, which can cause fibrin clot production. FIG. 3C is a broken side view of the entire guidewire 200, showing placement of the handle 234 on the proximal end (unnumbered). FIG. 3D is a cross section taken through the lines 3D-3D of the guidewire shown in FIGS. 3-3A, showing the tapered section 208 of the actuating member 206. FIG. 3D is a lateral cross section of the guidewire 200 illustrating the locations of the non-expandable side 238 and expandable side 240.

FIGS. 4-4B show a further embodiment of the invention. A guidewire 300 is similar to the guidewire 200 shown in FIG. 3 with the difference being the presence of a flat section 308 of the actuating member 306 corresponding with the distal section 304. The flat section 308 functions to lessen and more precisely control the amount of distal force required to place the guidewire 300 into a curved configuration (not shown), while also adding an additional degree of control regarding the actual direction of deflection. It will be observed that the distal section 304 is also defined by an open wound section 314 distal section of the coil 302 being less closely wound, or open wound. The open wound coil section 314 functions to further lessen and more precisely control the amount of longitudinal force required to place the guidewire 300 into a deflected configuration (not shown).

Figure 4D:
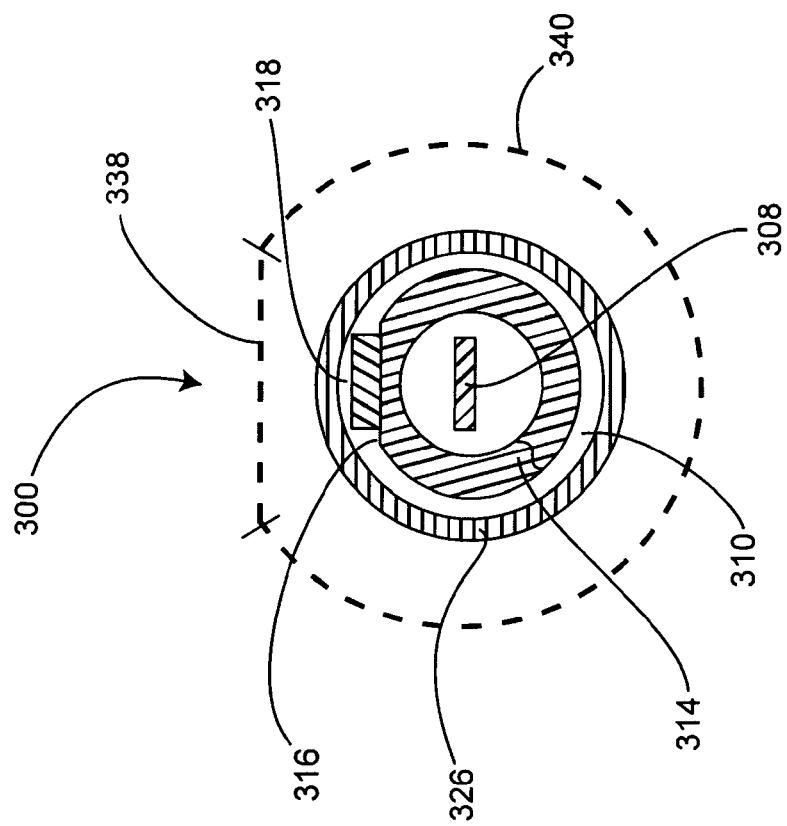
FIG. 4D is a cross section of the guidewire shown in FIG. 4 taken through the lines 4D-4D.
Figure 4C:
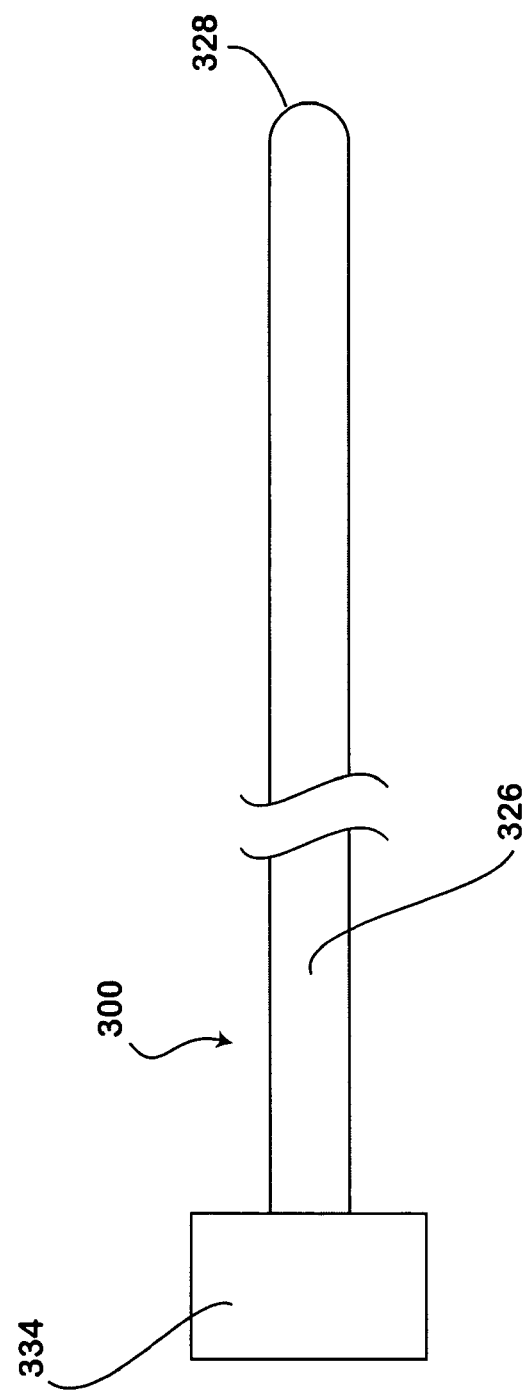
FIG. 4C is a broken side view of the guidewire shown in FIG. 4.

An actuating member 306 extends substantially the length of the guidewire 300 through a central space 310 defined inside the coil winds (unnumbered) and is proximally connected to a handle 334 (as shown in FIG. 4C) which allows control by an operator and is distally attached to a hemispherical end piece 327. As shown in FIGS. 4-4B, the end piece 327 is integrally attached to the actuating member 306, but may also be a separate, attached structure (not shown). The actuating member 306 can be made from a variety of materials having sufficient stiffness to be able to cause the distal section 304 to deflect and still be flexible enough to curve with the coil 302, including but not limited to stainless steel alloys, nickel titanium alloys and reinforced polymeric materials such as Kevlar® or fabric materials. In one embodiment, the coil 302 can be made from a radiopaque material such as a platinum-nickel alloy that allows the physician to visualize the position of the coil 302 thereby allowing precise navigation of the guidewire 300 into desired pathways with minimal rotational or reverse motion. A distal section 304 is defined by a ribbon 318. It will be observed that the distal section 304 is also defined by an open wound section 314 of the coil 302 which is less closely wound, or has a lesser pitch than a proximal section (unnumbered). The open wound coil section 314 functions to further lessen and more precisely control the amount of longitudinal force required to place the guidewire 300 into a deflected configuration (not shown). The ribbon 318 is fixedly attached to, and at least partially resides on, a flattened section 316 configured into an outer surface (unnumbered) of the coil 302 and functions to bind together the portions of the coil 302 to which it is attached. Means of attaching the ribbon 318 to the flattened section 316 include but are not limited to adhesives, laser welding, or soldering. The ribbon 318 is made of a suitable metallic material such as an austenitic stainless steel alloy or tungsten alloy, such as tungsten-molybdenum and tungsten-rhenium. In some instances iridium is added to the alloy, to increase strength and radiopaqueness. In another embodiment (not shown) the ribbon 318 is not used and instead the strong side (unnumbered) of the distal section 304 is defined by a series of welds (not shown), gluing (not shown) or mechanical fasteners (not shown) affixed to the coil winds. In an alternative embodiment (not shown), the ribbon 318 is replaced by application of a polymer fiber fused to coil 302. The fiber (not shown) is entangled into coil 302 by means of weaving in and out of the coil 302 winds and looping around the individual coil winds to form a solid attachment after application of an adhesive. In another embodiment (not shown) the distal section 304 is defined by a series of welds (not shown), gluing (not shown) or mechanical fasteners (not shown) affixed to the coil winds. In yet another embodiment (not shown) the ribbon 318 comprises a length of high strength adhesive tape affixed to the flattened section 316.

As shown in FIG. 4A, when distal force is applied to the actuating member 306 by the operator, the distal section 304 will deflect toward the proximal end (not shown), due to the non-expandable side 338 of the coil 302 to which the ribbon 318 is attached being unable to expand while allowing the expandable side 340 to expand, resulting in the distal section 304 assuming a deflected configuration. As shown in FIG. 4B, if proximal force is applied to the actuating member 306 the distal section 304 will deflect in the opposite direction as when distal force is applied. This is due to the pitch of the coil 302 having a relatively loose or open pitch to the coil winds (unnumbered), which allows the coil winds (unnumbered) on the expandable side 340, to be forced into a closer configuration. If the actuating member 306 is coupled with an actuating mechanism (not shown) such as a vernier type mechanism (not shown) a predictable and variable amount of curvature can be achieved with the application of a given amount of distal force. A coating 326 such as non-thrombogenic polymers, PTFE, ePTFE, FEP, polyester, polyurethane, polyethylene, silicone or hydrophilic may be applied over the coil 302 and hemispherical end piece 327 to improve sterility as well as enhancing the outer smoothness of the guidewire 300, thereby causing less trauma to the patient during introduction, the procedure itself and removal. In one embodiment the coating 326 is applied to the coil 302 by applying a polymer heat shrink tubing such as a PTFE, FEP, or polyester, followed by the application of a proper amount of heat or an appropriate length of time. In additional embodiments the coating 326 is applied by dipping the guidewire 300 into a dispersion polymer such as urethane or silicone, by spraying a polymer such as PTFE, FEP, polyester or silicone or by a co-extrusion process of a polymer such as PTFE, FEP, polyester, urethane or silicone. An additional advantage of a coating 326 is a reduction in adverse reactions due to repulsion of platelets, proteins, cells or other fouling materials, which can cause fibrin clot production. FIG. 4C is a broken side view of the entire guidewire 300, showing placement of the handle 334 on the proximal end (unnumbered). FIG. 4D is a lateral cross section taken through the lines 4D-4D of the guidewire shown in FIGS. 4D-4D, showing the flat section 308 of the actuating member 306. FIG. 4D further illustrates the locations of the non-expandable side 338 and expandable side 340.

FIG. 5 is a cross sectional centerline view taken along the longitudinal axis of a guidewire 800 having a preformed distal section 806 in a deflected, unstressed configuration. A coil 804 extends substantially the length of the guidewire 800 and has a close wound proximal section (unnumbered) which provides a degree of stiffness and stability necessary to navigate and introduce the guidewire 800 into a patient. It is seen that the continuous coil 804 has a distal section 806 wherein the coil 804 is open wound. In one embodiment, the coil 804 can be made from a radiopaque material such as a platinum-nickel alloy that allows the physician to visualize the position of the coil 804 thereby navigating the guidewire 800 into desired vascular pathways with minimal rotational or reverse motion. A ribbon 818 is fixedly attached to, and at least partially resides in, a flattened section 816 configured into an outer surface (unnumbered) of the coil 804 and functions to bind together the portions of the coil 804 to which it is attached, creating a non-expandable side 838. Means of attaching the ribbon 818 to the flattened section 816 include but are not limited to adhesives, laser welding, or soldering. The ribbon 818 is made of a suitable metallic material such as an austenitic stainless steel alloy or tungsten alloy, such as tungsten-molybdenum and tungsten-rhenium. In some instances iridium is added to the alloy, to increase strength and radiopaqueness. In another embodiment (not shown) the ribbon 818 is not used and instead the strong side (unnumbered) of the distal section 806 is defined by a series of welds (not shown), gluing (not shown) or mechanical fasteners (not shown) affixed to the coil winds. In an alternative embodiment (not shown), the ribbon 818 is replaced by application of a polymer fiber fused to coil 804. The fiber (not shown) is entangled into coil 804 by means of weaving in and out of the coil 804 winds and looping around the individual coil winds to form a solid attachment after application of an adhesive. In another embodiment (not shown) the distal section 806 is defined by a series of welds (not shown), gluing (not shown) or mechanical fasteners (not shown) affixed to the coil winds. In yet another embodiment (not shown) the ribbon 818 comprises a length of high strength adhesive tape affixed to the flattened section 816. In yet another embodiment (not shown) the distal section 806 comprises a non-expandable section bound by a length of high strength adhesive tape (not shown) affixed to the flattened section 816.

The coil 804 defines a central space 812 which an actuating member 802 movably extends through. The actuating member 802 is attached at its distal end (unnumbered) to a hemispherical end piece 810 which is also attached to the distal termination (unnumbered) of the coil 804. As shown in FIGS.

5 and 5A, the end piece 810 is integrally attached to the actuating member 802, but may also be a separate, attached structure (not shown). A coating 808 such as non-thrombogenic polymers, PTFE, ePTFE, FEP, polyester, polyurethane, polyethylene, silicone or hydrophilic may be applied over the coil 804 and hemispherical end piece 810 to improve sterility as well as enhancing the outer smoothness of the guidewire 800, thereby causing less trauma to the patient during introduction, the procedure itself and removal. In one embodiment the coating 808 is applied to the coil 804 by applying a polymer heat shrink tubing such as a PTFE, FEP, or polyester, followed by the application of a proper amount of heat or an appropriate length of time. In additional embodiments the coating 808 is applied by dipping the guidewire 800 into a dispersion polymer such as urethane or silicone, by spraying a polymer such as PTFE, FEP, polyester or silicone or by a co-extrusion process of a polymer such as PTFE, FEP, polyester, urethane or silicone.

Figure 5B:
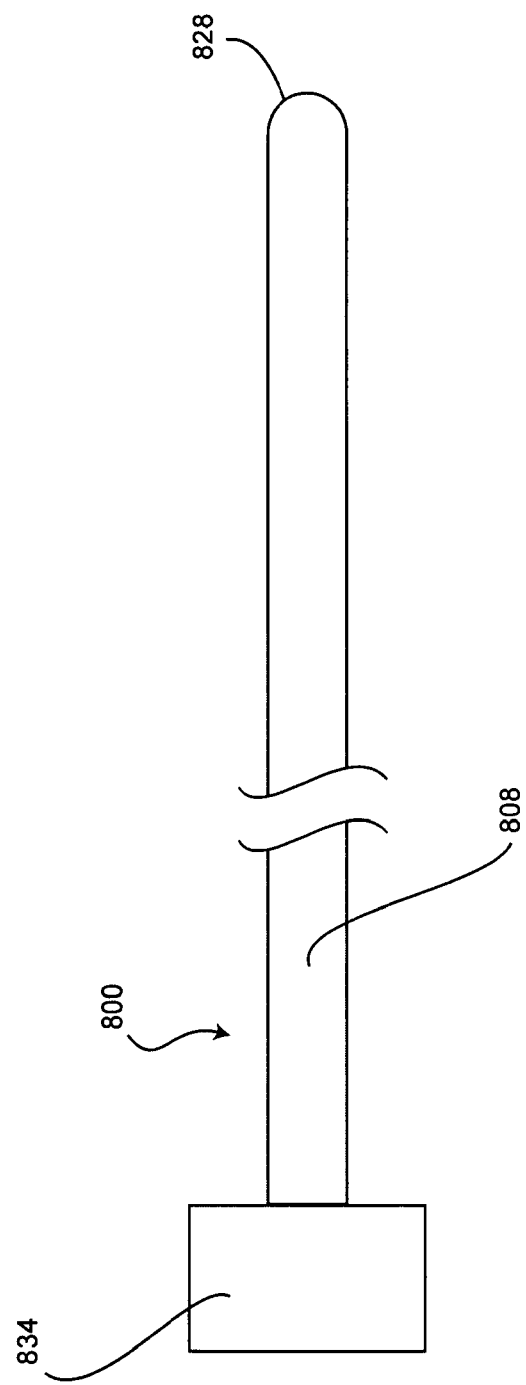
FIG. 5B is a broken side view of the guidewire shown in FIGS. 5 and 5A.
Figure 5C:
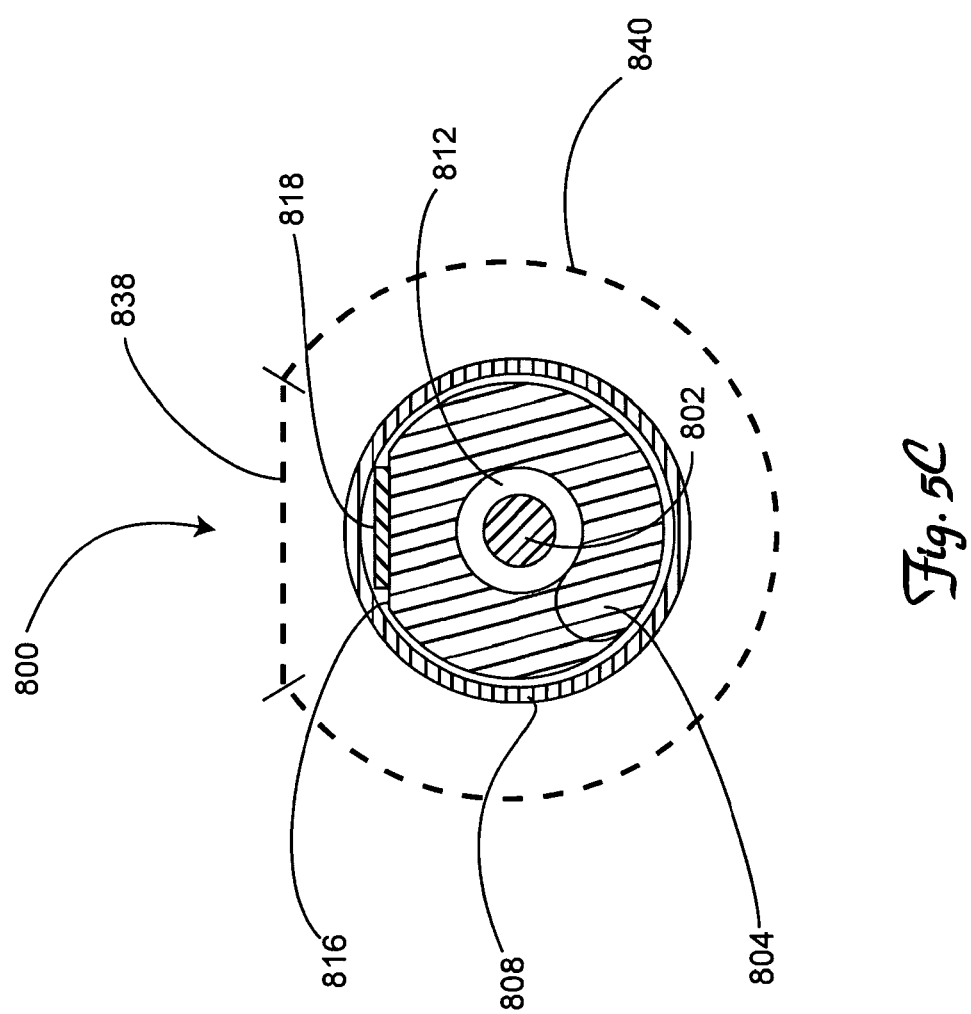
FIG. 5C is a cross section of the guidewire shown in FIG. 5 taken through the lines 5C-5C.

FIG. 5A is a cross sectional centerline view taken along the longitudinal axis of the guidewire 800 shown in FIG. 5 wherein the preformed distal section 806 is in the straightened, stressed configuration as a result of proximal force being applied to the actuating member 802. In one embodiment the actuating member 802 is coupled with an actuating mechanism (not shown) such as a vernier type mechanism (not shown) allowing a predictable and variable degree of curvature to be achieved with the application of a given amount of distal force. This allows the physician to adjust the degree of curvature of the distal section 806 or use the preformed, curved distal section 806 to hold or anchor the guidewire 800 in a desired location. When an adequate amount of longitudinal force is applied to the actuating member 802 the guidewire 800 will be completely straightened allowing the physician to traverse straight sections of vasculature as well as providing stiffness to pierce through lesions when required. FIG. 5B is a broken side view of the entire guidewire 800, showing placement of the handle 834 on the proximal end (unnumbered). FIG. 5C is a lateral cross section of the guidewire 800 illustrating the locations of the non-expandable side 838 and the expandable side 840.

Figure 6:
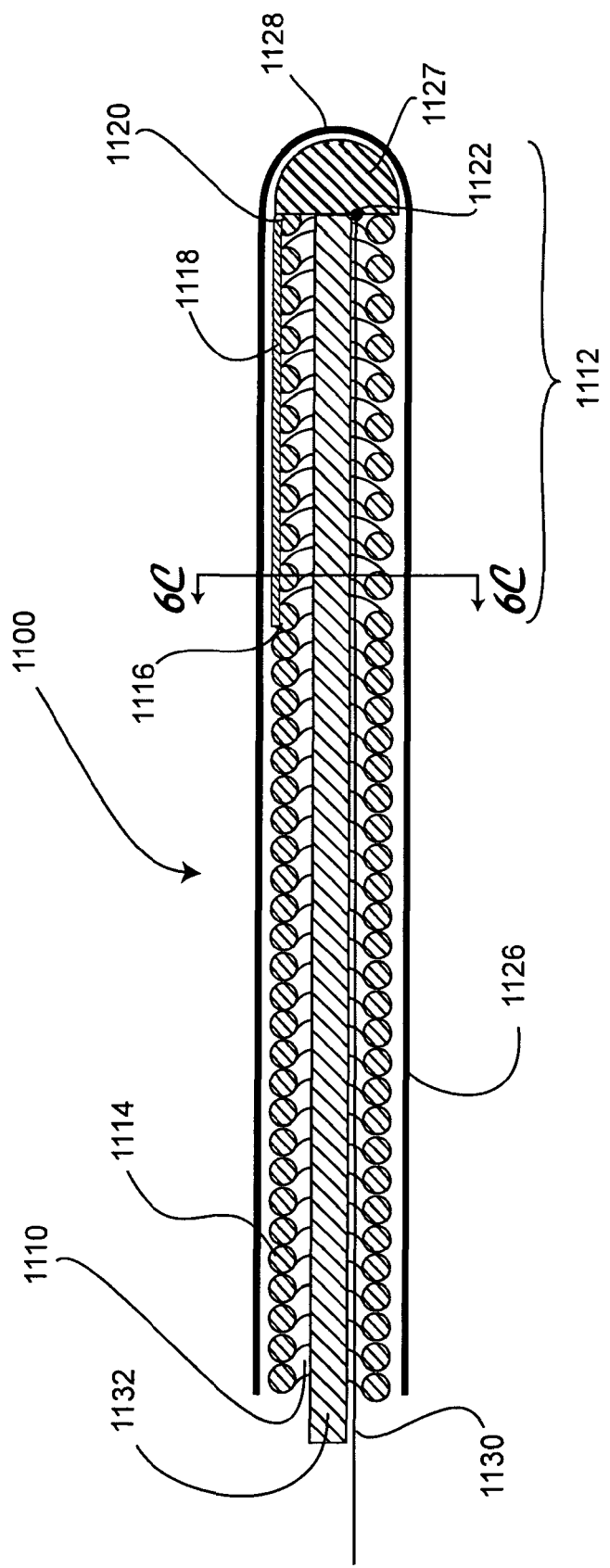
FIG. 6 is a cross sectional centerline view taken along the longitudinal axis of a guidewire of the present invention having a deflected distal section in an unstressed, straight configuration.
Figure 6A:
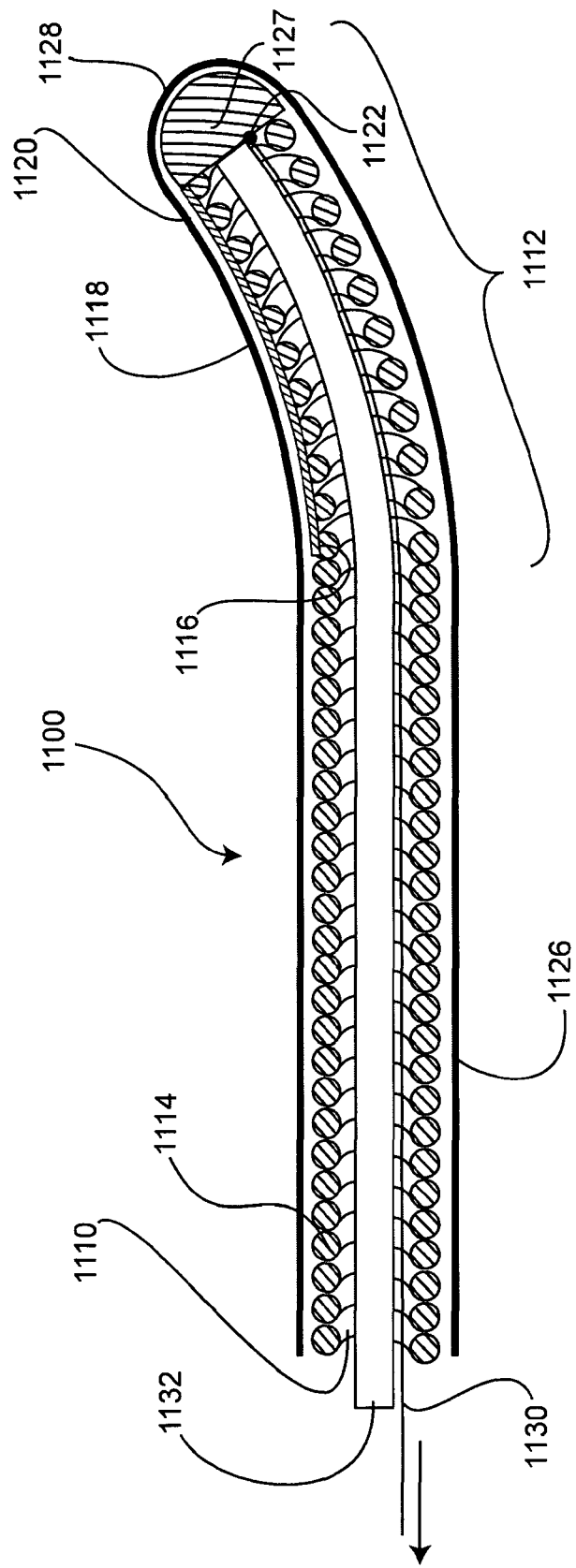
FIG. 6A is a cross sectional centerline view taken along the longitudinal axis of the guidewire shown in FIG. 6, following the application of proximal force, in a stressed, deflected configuration.

FIG. 6 is a cross sectional centerline view taken along the longitudinal axis of a guidewire 1100 of the present invention. The guidewire 1100 has a filamentous or metal (not shown) actuating member 1130 attached 1122 to a distal end 1120 of a coil 1114 enabling the guidewire 1100 to deflect as shown in FIG. 6A upon proximal force being applied to the actuating member 1130. The coil 1114 extends between a distal end 1120 and a proximal end (not shown) and defines a central space 1110 inside the coil 1114. The coil 1114 further defines a flattened section 1116 towards the distal end 1120 which is configured to receive a ribbon 1118 which is affixed to the coil 1114. The ribbon 1118 is made of a suitable metallic material such as austenitic stainless steel or tungsten alloys such as tungsten-molybdenum and tungsten-rhenium and functions to bind together the side of the coil 1114 to which it is attached. Means of attaching the ribbon 1118 to the flattened section 1116 include but are not limited to adhesives, laser welding, or soldering. In another embodiment (not shown) the ribbon 1118 is not used and instead the distal section 1112 is defined by a series of welds (not shown), gluing (not shown) or mechanical fasteners (not shown) affixed to the coil winds (unnumbered). In an alternative embodiment (not shown), the ribbon 1118 is replaced by application of a polymer fiber fused to coil 1114 which could be made of a similar material as actuating member 1130. The fiber (not shown) is entangled into coil 1114 by means of weaving in and out of the coil 1114 winds and looping around the individual coil winds to form a solid attachment after application of an adhesive. In yet another embodiment (not shown) the ribbon 1118 comprises a length of high strength adhesive tape affixed to the flattened section 1116.

Figure 6B:
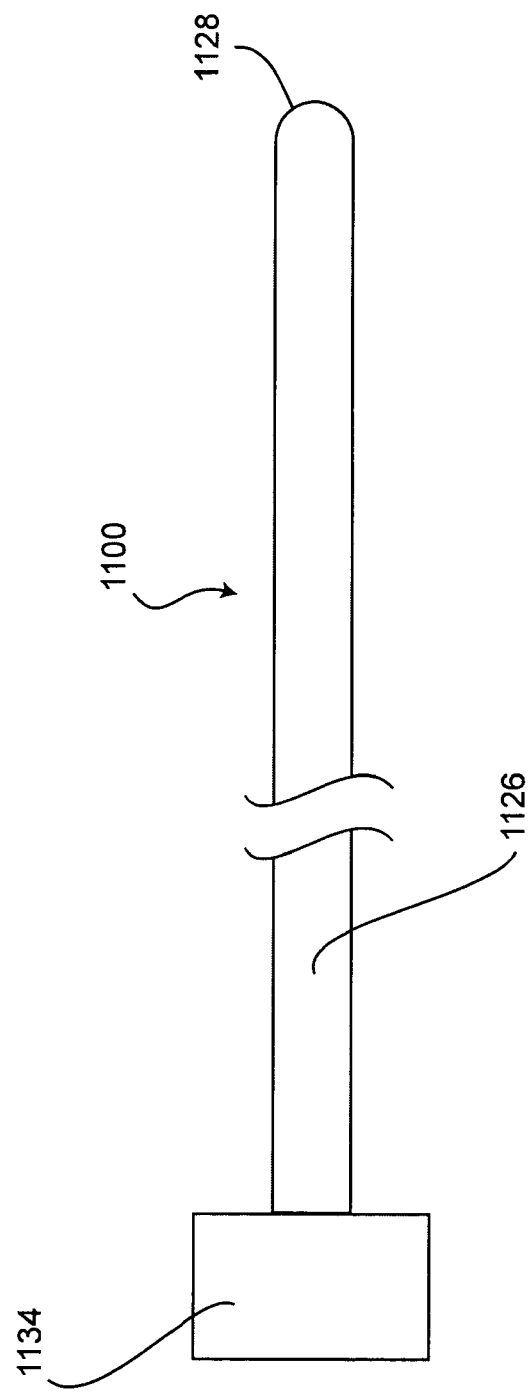
FIG. 6B is a broken side view of the guidewire shown in FIG. 6.
Figure 6C:
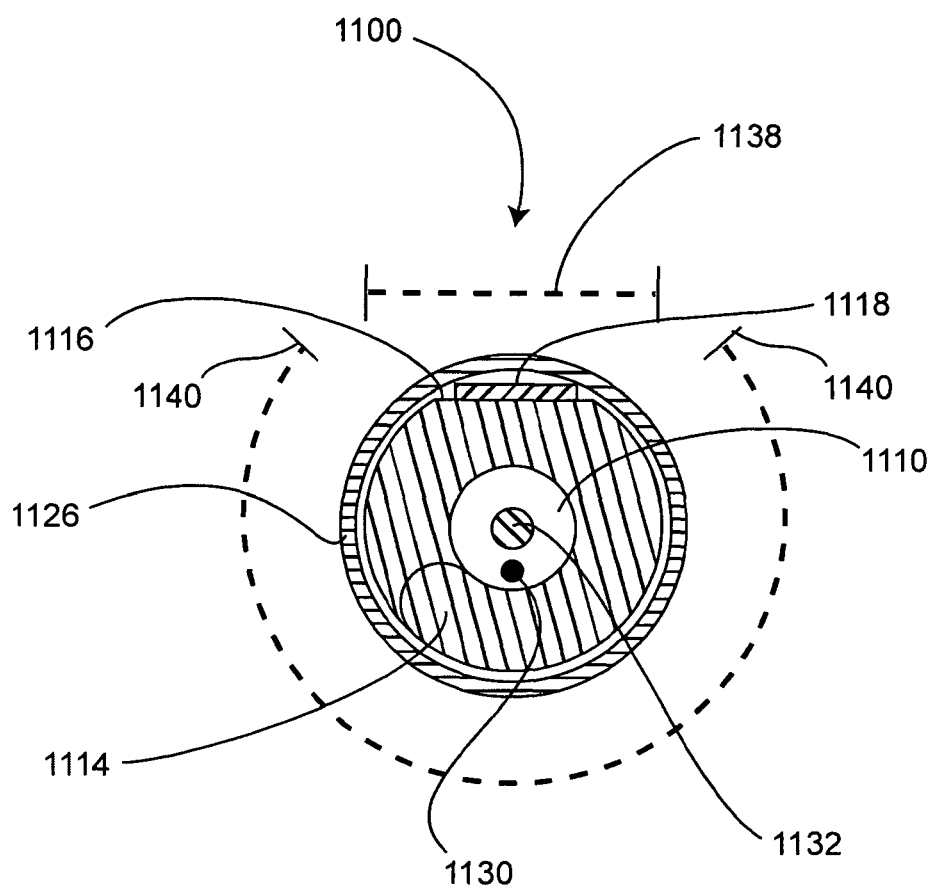
FIG. 6C is a cross section of the guidewire shown in FIG. 6 taken through the lines 6C-6C.

As shown in FIG. 6A, when proximal force is applied to the actuating member 1130, the distal section 1112 deflects due to the non-expandable side 1138 of the coil 1114 to which the ribbon 1118 is attached being prevented from expanding while allowing the expandable side 1140 to be placed into a configuration where the coil winds (unnumbered) are forced closer together. This results in the distal section 1112 deflecting from an unstressed, straight configuration. If the actuating member 1130 is coupled with an actuating mechanism (not shown) such as a vernier type mechanism (not shown), a predictable and variable amount of deflection can be achieved with the application of a given amount of proximal force. It is also observed that along the distal section 1112 of the coil 1114 the coil is wound in a looser or more open pitch than the remainder of the coil 1114, imparting a greater degree of flexibility to the distal section 1112. A hemispherical end piece 1127 is attached to the distal end (unnumbered) of the core wire 1132, which resides inside the central space 1110 and extends the length of the guidewire 1100. The core wire 1132 is also attached to the coil 1114 at the distal end 1120. As shown in FIGS. 6-6A, the end piece 1127 is integrally attached to the core wire 1132, but may also be a separate, attached structure (not shown). It should be noted that in this embodiment, the core wire 1132 has a constant diameter. The core wire 1132 functions to add stiffness and stability to the guidewire 1100 for applications requiring such characteristics. The actuating member 1130 can be made of a polymeric material such as Kevlar® or other suitable metallic material such as austenitic stainless steel alloys or tungsten alloys, such as tungsten-molybdenum and tungsten-rhenium. The actuating member 1130 is attached 1122 to the distal end 1120 of the coil 1114 and routed through the central space 1110 so as to be able to apply proximal force to the distal section 1112, allowing an operator to precisely deflect the distal section 1112 thereby enhancing the steerability and overall maneuverability of the guidewire 1100. A coating 1126 such as non-thrombogenic polymers, PTFE, ePTFE, FEP, polyester, polyurethane, polyethylene, silicone or hydrophilic may be applied over the coil 1114 and hemispherical end piece 1127 to improve sterility as well as enhancing the outer smoothness and increase slipperiness as well as partially binding the other components of the guidewire 1100 together, thereby causing less trauma to the patient during introduction, the procedure itself and removal. An additional advantage to a coating 1126 is a reduction in adverse reactions due to repulsion of platelets, proteins, cells or other fouling materials, which can cause fibrin clot production. FIG. 6B is a broken side view of the entire guidewire 1100, showing placement of the handle 1134 on the proximal end (unnumbered). FIG. 6C is a lateral cross section of the guidewire 1100 taken through the lines 6C-6C and illustrates the locations of the non-expandable side 1138 and the expandable side 1140.

FIG. 7 is a cross sectional centerline view taken along the longitudinal axis of a guidewire 1200 of the present invention having a filamentous or metal (not shown) actuating member 1230 attached to a distal end 1220 of a coil 1214, enabling the guidewire 1200 to deflect to an alternative shape upon proximal force being applied to the actuating member 1230. The coil 1214 extends between the distal end 1220 and a proximal end (not shown) and defines a central space 1210 inside the coil winds. The coil 1214 further defines a flattened section 1216 towards the distal end 1220 which is configured to receive a ribbon 1218 which is affixed to the coil 1214. The ribbon 1218 is made of a suitable metallic material such as austenitic stainless steel alloys or tungsten alloys, such as tungsten-molybdenum and tungsten-rhenium. The ribbon 1218 functions to bind together the side of the coil 1214 to which it is attached, creating a non-expandable side 1238 and an expandable side 1240. Means of attaching the ribbon 1218 to the flattened section 1216 include but are not limited to adhesives, laser welding, or soldering. In another embodiment (not shown) the ribbon 1218 is not used and instead the distal section 1212 is defined by a series of welds (not shown), gluing (not shown) or mechanical fasteners (not shown) affixed to a side of the coil winds. In an alternative embodiment (not shown), the ribbon 1218 is replaced by application of a polymer fiber fused to coil 1214 which can include a polymer fiber of a similar material as the actuating member 1230. The fiber (not shown) is entangled into coil 1214 by means of weaving in and out of the coil 1214 winds and looping around the individual coil winds to form a solid attachment after application of an adhesive. In yet another embodiment (not shown) the ribbon 1218 comprises a length of high strength adhesive tape affixed to the flattened section 1216.

As shown in FIG. 7A, when proximal force is applied to the actuating member 1230 by the operator, the distal section 1212 deflects due to the non-expandable side 1238 of the coil 1214 to which the ribbon 1218 is attached being prevented from expanding while allowing the expandable side 1240 to expand, resulting in the distal section 1212 deflecting from an unstressed, straight configuration. If the actuating member 1230 is coupled with an actuating mechanism (not shown) such as a vernier type mechanism (not shown) a predictable and variable amount of deflection can be achieved with the application of a given amount of proximal force. It is also observed that along the distal section 1212 of the coil 1214 the coil is wound at a lesser or looser pitch than the remainder of the coil 1214, imparting a greater degree of flexibility to the distal section 1212. A hemispherical end piece 1227 is attached to the distal end 1220 of the core wire 1232, which resides inside the central space 1210 and extends the length of the guidewire 1200. The core wire 1232 is also attached to the coil 1214 at the distal end 1220. It should be noted that in this embodiment, the core wire 1232 has a gradually tapering diameter along the distal section 1212, which lessens and gives a further degree of precision in the amount of proximal force required to deflect the guidewire 1200. The core wire 1232 functions to add stiffness and stability to the guidewire 1200 for applications requiring such characteristics. The actuating member 1230 can be made of a polymeric material such as Kevlar® or other suitable metallic material such as austenitic stainless steel alloys or tungsten alloys, such as tungsten-molybdenum and tungsten-rhenium. The actuating member 1230 is attached 1222 to the distal end 1220 of the coil 1214 and routed through the central space 1210 so as to be able to transfer proximal force to the distal section 1212, allowing an operator to precisely deflect the distal section 1212 thereby enhancing the steerability and overall maneuverability of the guidewire 1200. A coating 1226 such as non-thrombogenic polymers, PTFE, ePTFE, FEP, polyester, polyurethane, polyethylene, silicone or hydrophilic may be applied over the coil 1214 and hemispherical end piece 1227 to improve sterility as well as enhancing the outer smoothness of the guidewire 1200, thereby causing less trauma to the patient during introduction, the procedure itself and removal. In one embodiment the coating 1226 is applied to the coil 1214 by applying a polymer heat shrink tubing such as a PTFE, FEP, or polyester, followed by the application of a proper amount of heat or an appropriate length of time. In additional embodiments the coating 1226 is applied by dipping the guidewire 1200 into a dispersion polymer such as urethane or silicone, by spraying a polymer such as PTFE, FEP, polyester or silicone or by a co-extrusion process of a polymer such as PTFE, FEP, polyester, urethane or silicone. An additional advantage of a coating 1226 is a reduction in adverse reactions due to repulsion of platelets, proteins, cells or other fouling materials, which can cause fibrin clot production. FIG. 7B is a broken side view of the entire guidewire 1200, showing placement of the handle 1236 on the proximal end (unnumbered). FIG. 7C is a lateral cross section of the guidewire 1200 taken through the lines 7C-7C and illustrates the locations of the non-expandable side 1238 and expandable side 1240.

FIG. 8 is a cross sectional centerline view taken along the longitudinal axis of a guidewire 1300 of the present invention having a filamentous or metal (not shown) actuating member 1330 attached to a distal end 1320 of a coil 1314 enabling the guidewire 1300 to deflect to an alternative shape upon proximal force being applied to the actuating member 1330. The coil 1314 extends between a distal end 1320 and a proximal end (not shown) and defines a central space 1310 inside the coil winds (unnumbered). The coil 1314 further defines a flattened section 1316 towards the distal end 1320 which is configured to receive a ribbon 1318 which is thereat affixed to the coil 1314. The ribbon 1318 is made of a suitable metallic material such as austenitic stainless steel alloys or tungsten alloys, such as tungsten-molybdenum and tungsten-rhenium. The ribbon 1318 functions to bind together the side of the coil 1314 to which it is attached, creating a non-expandable side 1338 and an expandable side 1340. Means of attaching the ribbon 1318 to the flattened section 1316 include but are not limited to adhesives, laser welding, or soldering. In another embodiment (not shown) the ribbon 1318 is not used and instead the distal section 1312 is defined by a series of welds (not shown), gluing (not shown) or mechanical fasteners (not shown) affixed to the coil winds. In an alternative embodiment (not shown), the ribbon 1318 is replaced by application of a polymer fiber fused to coil 1314 which can include a polymer fiber of a similar material as the actuating member 1330. The fiber is entangled into the coil 1314 by means of weaving in and out of the coil 1314 winds and looping around the individual coil winds to form a solid attachment after application of an adhesive. In yet another embodiment (not shown) the ribbon 1318 comprises a length of high strength adhesive tape affixed to the flattened section 1316.

Figure 8A:
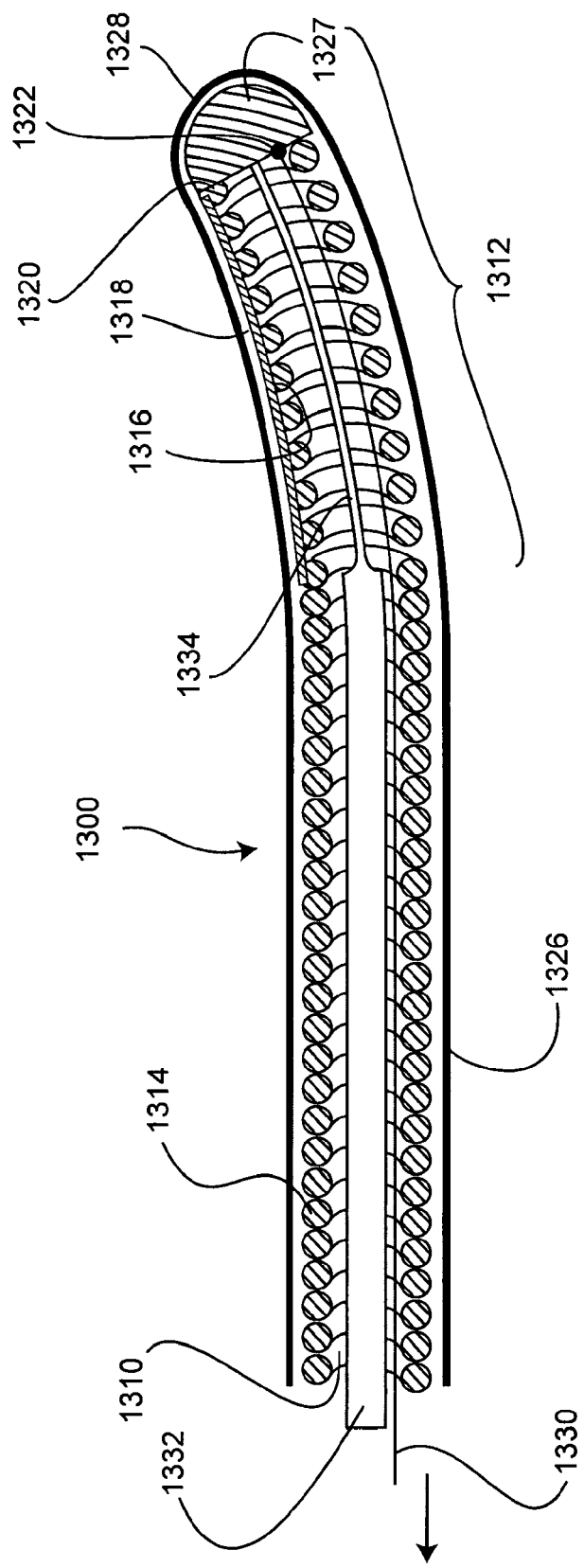
FIG. 8A is a cross sectional centerline view taken along the longitudinal axis of the guidewire shown in FIG. 8, following the application of proximal force, in a deflected configuration.
Figure 8B:
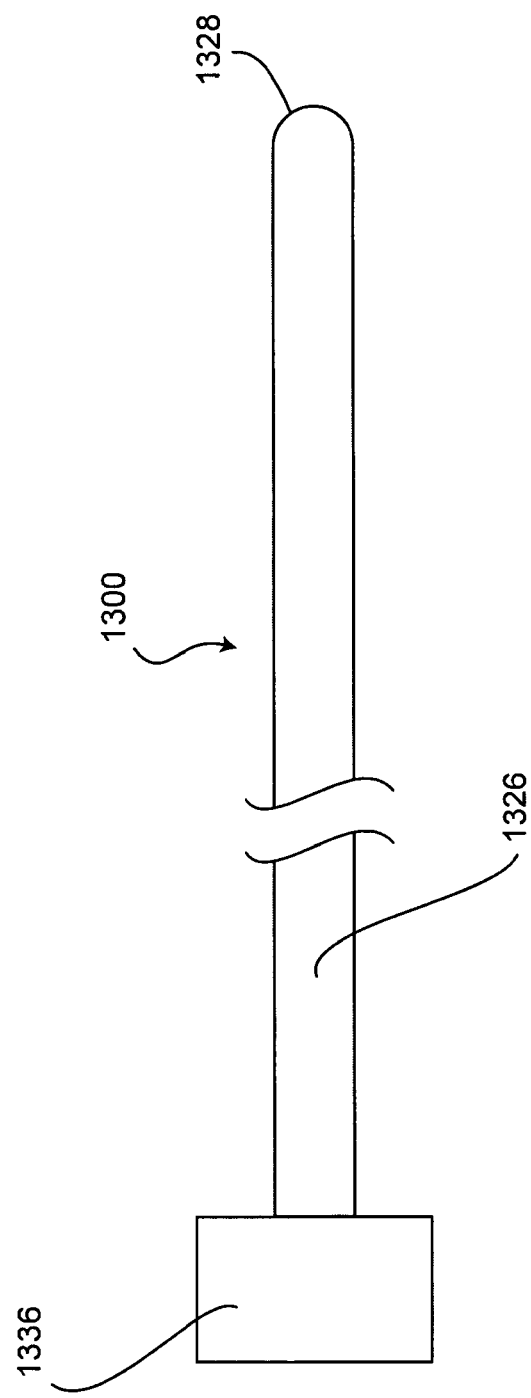
FIG. 8B is a broken side view of the guidewire shown in FIG. 8.

As shown in FIG. 8A, when proximal force is applied to the actuating member 1330 by the operator, the distal section 1312 will deflect due to the non-expandable side 1338 of the coil 1314, to which the ribbon 1318 is attached, being prevented from expanding while allowing the expandable side 1340 to expand. If the actuating member 1330 is coupled with an actuating mechanism (not shown) such as a vernier type mechanism (not shown) a predictable and variable amount of deflection can be achieved with the application of a given amount of proximal force. It is also observed that along the distal section 1312 of the coil 1314 the coil is wound at a more open or looser pitch than the remainder of the coil 1314, imparting a greater degree of flexibility to the distal section 1312. A hemispherical end piece 1327 is attached to the distal end (unnumbered) of the core wire 1332, which resides inside the central space 1310 and extends the length of the guidewire 1300. The core wire 1332 is also attached to the coil 1314 at the distal end 1320. The core wire 1332 functions to add stiffness and stability to the guidewire 1300 for applications requiring such characteristics. It should be noted that in this embodiment, the core wire 1332 has a flat section 1334 along the distal section 1312, which gives a further degree of precision in the amount of proximal force required to deflect the guidewire 1300, while also adding an additional degree of control regarding the actual direction of deflection. The actuating member 1330 can be made of a polymeric material such as Kevlar® or other suitable metallic material such as austenitic stainless steel alloys or tungsten alloys, such as tungsten-molybdenum and tungsten-rhenium and is attached 1322 to the distal end 1320 of the coil 1314 and routed through the central space 1310 so as to be able to apply proximal force to the distal section 1312, allowing an operator to precisely deflect the distal section 1312 thereby enhancing the steerability and overall maneuverability of the guidewire 1300. A coating 1326 such as non-thrombogenic polymers, PTFE, ePTFE, FEP, polyester, polyurethane, polyethylene, silicone or hydrophilic may be applied over the coil 1314 and hemispherical end piece 1327 to improve sterility as well as enhancing the outer smoothness of the guidewire 1300, thereby causing less trauma to the patient during introduction, the procedure itself and removal. In one embodiment the coating 1326 is applied to the coil 1314 by applying a polymer heat shrink tubing such as a PTFE, FEP, or polyester, followed by the application of a proper amount of heat or an appropriate length of time. In additional embodiments the coating 1326 is applied by dipping the guidewire 1300 into a dispersion polymer such as urethane or silicone, by spraying a polymer such as PTFE, FEP, polyester or silicone or by a co-extrusion process of a polymer such as PTFE, FEP, polyester, urethane or silicone. An additional advantage of a coating 1326 is a reduction in adverse reactions due to repulsion of platelets, proteins, cells or other fouling materials, which can cause fibrin clot production. FIG. 8B is a broken side view of the entire guidewire 1300, showing placement of the handle 1336 on the proximal end (unnumbered).

It is contemplated that the ribbon 18, 118, 218, 318, 818, 1118, 1218, 1318 is made of a radiopaque material which is used by the physician to visualize the distal end 28, 128, 228, 328, 828, 1128, 1128, 1328 of the guidewire 10, 100, 200, 300, 800, 1100, 1200, 1300. As the ribbon 18, 118, 218, 318, 818, 1118, 1218, 1318 is long and slender, the physician will not only know where the distal end 28, 128, 228, 328, 828, 1128, 1128, 1328 is, but also which way the distal end 28, 128, 228, 328, 828, 1128, 1128, 1328 will bend when the guidewire is actuated which will, in turn, assist with navigating the guidewire 10, 100, 200, 300, 800, 1100, 1200, 1300 through tortuous vascular anatomy.

The outer diameter of the guidewire 10, 100, 200, 300, 800, 1100, 1200, 1300 is manufactured to dimensions that are industry standards for intravenous interventions and can range from between approximately 0.010 inch to 0.055 inch which allows passage through a five French catheter at 0.066 inch outer diameter, as an example. The length of the guidewire 10, 100, 200, 300, 800, 1100, 1200, 1300 is similarly manufactured to conform to industry standards and may range between approximately 10 centimeters to 300 centimeters as required by the particular medical procedure.

Making the guidewire 10, 100, 200, 300, 800, 1100, 1200, 1300 of the present invention requires first creating the coil/ribbon subassembly (not shown). Wire having a diameter between approximately 0.0015 and 0.003 inches is formed into a coil 14, 102, 202, 302, 804, 1114, 1214, 1314 using a coil winding machine well known to those having skill in the art. Next, the coil 14, 102, 202, 302, 804, 1114, 1214, 1314 is placed into a fixture where the individual coil winds are firmly immobilized without being deformed or damaged in any other way. The fixture and immobilized coil 14, 102, 202, 302, 804, 1114, 1214, 1314 is then inserted into an electrical discharge machine (EDM) where the flattened area 16, 116, 216, 316, 816, 1116, 1216, 1316 is machined into a side of the coil 14, 102, 202, 302, 804, 1114, 1214, 1314. Following creation of the flattened area 16, 116, 216, 316, 816, 1116, 1216, 1316, the fixture and immobilized coil 14, 102, 202, 302, 804, 1114, 1214, 1314 is placed into a machine which positions the ribbon 18, 118, 218, 318, 818, 1118, 1218, 1318 over the flattened area 16, 116, 216, 316, 816, 1116, 1216, 1316. In one embodiment, the ribbon 18, 118, 218, 318, 818, 1118, 1218, 1318 is laser welded onto the flattened area 16, 116, 216, 316, 816, 1116, 1216, 1316 wherein it is permanently affixed. In other embodiments, as described above, the ribbon 18, 118, 218, 318, 818, 1118, 1218, 1318 may be adhered to the flattened area 16, 116, 216, 316, 816, 1116, 1216, 1316 by other means known to those having skill in the art. In yet other embodiments, as described above, the coil 14, 102, 202, 302, 804, 1114, 1214, 1314 is removed from the fixture and a filamentous polymeric fiber (not shown) is affixed to the coil winds in the area that is to become the distal section 12, 104, 204, 304, 806, 1112, 1212, 1312. When the ribbon 18, 118, 218, 318, 818, 1118, 1218, 1318 is affixed to the flattened area 16, 116, 216, 316, 816, 1116, 1216, 1316 of the coil 14, 102, 202, 302, 804, 1114, 1214, 1314, the coil/ribbon subassembly is completed.

The actuating member 30, 130, 206, 306, 802 or core wire 1132, 1232, 1332 can be made as an integral part by centerless grinding. In an alternative embodiment, a separate shaft is attached to an end piece by swaging, adhesives or using an interference fit.

The actuating member 30, 130, 206, 306, 802 or core wire 1132, 1232, 1332 is inserted through the central space 36a, 36b, 110, 210, 310, 812, 1110, 1210, 1310 through the distal section 12, 104, 204, 304, 806, 1112, 1212, 1312 of the coil 14, 102, 202, 302, 804, 1114, 1214, 1314 and affixed to the coil 14, 102, 202, 302, 804, 1114, 1214, 1314 by laser welding. The guidewire 10, 100, 200, 300, 800, 1100, 1200, 1300 is next coated using the various methods as described above, followed by curing the coating 26, 126, 226, 326, 808, 1126, 1226, 1326 using methods and equipment well known to those skilled in the art. At this point, the guidewire 10, 100, 200, 300, 800, 1100, 1200, 1300 is completed and may be sterilized and packaged for shipment and eventual use.

USE

Using the guidewire 10, 100, 200, 300, 800, 1100, 1200, 1300 of the present invention first requires removal from sterile packaging. Standard surgical techniques are employed to incise the proper blood vessel or bodily duct followed by insertion of an introducer which provides a sealed entry port into the vessel. The guidewire 10, 100, 200, 300, 800, 1100, 1200, 1300 is then inserted into the introducer and carefully navigated through the patient's vasculature until the treatment site is reached. At that point, the procedure is performed. Upon completion of the procedure, the guidewire 10, 100, 200, 300, 800, 1100, 1200, 1300 is removed from the patient and disposed of.

While the invention as described above is most particularly directed to guidewires in the separate embodiments described herein, the invention may also be applied to a variety of medical devices capable of being introduced into the vasculature or other anatomy of a patient. For example, the invention may be applied to singular guidewires, catheters (e.g., balloon angioplasty, stent delivery, drug delivery, fluid delivery or fluid removal), conduit for artherectomy devices and IVUS catheters, laparoscopic and endoscopic devices, spinal or cranial navigation devices, embolic protection devices, therapeutic devices and other medical devices.

The invention claimed is:

1. A guidewire, comprising:
    a distal section having an expandable side and a non-expandable side, the distal section comprising a metallic coil defining a first central space and comprising a plurality of winds defined by a first outer radius when viewed in a longitudinal direction, and an external flat section on the plurality of winds defined by a second outer radius when viewed in the longitudinal direction, the second outer radius being smaller than the first outer radius;
    a proximal section comprising a hollow member defining a second central space coaxial with the first central space, the proximal section having less flexibility than the distal section;
    a metallic ribbon having a rectangular cross section attached to the external flat section at each of the plurality of winds; and
    an actuating member extending through the first central space and the second central space, the actuating member attached proximate a distal end of the distal section and capable of transferring longitudinal force to the coil.

2. The guidewire of claim 1 wherein the guidewire in a non-stressed configuration has a straight configuration.

3. The guidewire of claim 1 wherein the guidewire in a non-stressed configuration has a deflected configuration.

4. The guidewire of claim 1 wherein the actuating member is a solid rod defining a distal end and having an end piece attached to the distal end.

5. The guidewire of claim 4 wherein the actuating member defines a tapered section corresponding to the distal section.

6. The guidewire of claim 1 wherein the proximal section comprises a coil, and wherein the metallic coil of the distal section is wound at a lesser pitch than the coil of the proximal section.

7. The guidewire of claim 6 wherein the metallic coil of the distal section and the coil of the proximal section are integrally attached.

8. A guidewire comprising:
    a distal section having a longitudinal axis and comprising a coil defining a central space extending along the longitudinal axis, the coil comprising a plurality of winds having an external flat section; and
    a ribbon having a rectangular cross section attached to the external flat section at each of the plurality of winds,
    wherein when viewed in a cross section taken orthogonal to the longitudinal axis, the coil has a first outer radius and a second outer radius at the external flat section, the second outer radius being less than the first outer radius.

9. The guidewire of claim 8 wherein the ribbon is a metallic ribbon and the coil is a metallic coil.

10. The guidewire of claim 9 wherein the metallic ribbon is welded to the external flat section of the metallic coil.

11. The guidewire of claim 8 further comprising a proximal section extending along the longitudinal axis and defining a second central space coaxial with the central space of the distal section, the proximal section having less flexibility than the distal section.

12. The guidewire of claim 11 wherein the proximal section comprises a coil that is integrally attached to the coil of the distal section.

13. The guidewire of claim 11 further comprising an actuating member extending through the central space of the distal section and the second central space, the actuating member attached proximate a distal end of the distal section and capable of transferring longitudinal force to the coil.

14. A guidewire comprising:
    a distal section having a longitudinal axis and comprising a coil defining a central space extending along the longitudinal axis, the coil comprising a plurality of winds having an external flat section; and
    a ribbon having a rectangular cross section attached to the external flat section at each of the plurality of winds,
    wherein when viewed in a cross section taken orthogonal to the longitudinal axis, the coil has a first outer radius and the external flat section has a second outer radius, the second outer radius being less than the first outer radius.

15. The guidewire of claim 14 wherein the ribbon is a metallic ribbon and the coil is a metallic coil.

16. The guidewire of claim 15 wherein the metallic ribbon is welded to the external flat section of the metallic coil.

17. The guidewire of claim 14 further comprising a proximal section extending along the longitudinal axis and defining a second central space coaxial with the central space of the distal section, the proximal section having less flexibility than the distal section.

18. The guidewire of claim 17 wherein the proximal section comprises a coil that is integrally attached to the coil of the distal section.

19. The guidewire of claim 17 further comprising an actuating member extending through the central space of the distal section and the second central space, the actuating member attached proximate a distal end of the distal section and capable of transferring longitudinal force to the coil.

* * * * *